US009795675B2

(12) United States Patent
Da Silva Ferreira et al.

(10) Patent No.: US 9,795,675 B2
(45) Date of Patent: Oct. 24, 2017

(54) LIGHT-ACTIVATABLE POLYMERIC NANOPARTICLES

(71) Applicant: CNC—CENTRO DE NEUROCIÊNCIAS E BIOLOGIA CELULAR, Coimbra (PT)

(72) Inventors: Lino Da Silva Ferreira, Coimbra (PT); Carlos Samuel Marques Boto, São Romão (PT); Ricardo Neves Pires Das Neves, Aveiro (PT)

(73) Assignee: CNC — CENTRO DE NEUROCIÊNCIAS E BIOLOGIA CELULAR, Coimbra (PT)

( * ) Notice: Subject to any disclaimer, the term of this patent is extended or adjusted under 35 U.S.C. 154(b) by 0 days.

(21) Appl. No.: 15/021,167

(22) PCT Filed: Sep. 10, 2014

(86) PCT No.: PCT/IB2014/064399
§ 371 (c)(1),
(2) Date: Mar. 10, 2016

(87) PCT Pub. No.: WO2015/036939
PCT Pub. Date: Mar. 19, 2015

(65) Prior Publication Data
US 2016/0220673 A1    Aug. 4, 2016

(30) Foreign Application Priority Data
Sep. 10, 2013  (PT) .......................................... 107150

(51) Int. Cl.
| | | |
|---|---|---|
| *A61K 41/00* | (2006.01) |
| *A61K 8/84* | (2006.01) |
| *A61K 8/02* | (2006.01) |
| *A61K 9/51* | (2006.01) |
| *A61K 31/203* | (2006.01) |
| *A61K 31/538* | (2006.01) |

(52) U.S. Cl.
CPC ........ *A61K 41/0042* (2013.01); *A61K 8/0241* (2013.01); *A61K 8/84* (2013.01); *A61K 9/5146* (2013.01); *A61K 9/5161* (2013.01); *A61K 31/203* (2013.01); *A61K 31/538* (2013.01); *A61K 2800/5424* (2013.01); *A61K 2800/5426* (2013.01); *A61K 2800/56* (2013.01); *A61K 2800/81* (2013.01)

(58) Field of Classification Search
CPC .... A61K 41/0042; A61K 8/84; A61K 8/0241; A61K 9/5146; A61K 9/5161; A61K 31/203; A61K 31/538; A61K 2800/5424; A61K 2800/5426; A61K 2800/56; A61K 2800/81
See application file for complete search history.

(56) References Cited

U.S. PATENT DOCUMENTS 6,645,525 B1 * 11/2003 Woiszwillo .......... A61K 9/1641
264/4.1

FOREIGN PATENT DOCUMENTS

| KR | 20130022225 A | 3/2013 |
|---|---|---|
| WO | WO 01/01964 A2 | 1/2001 |
| WO | WO 2008/093195 A2 | 8/2008 |
| WO | WO 2011/145963 A1 | 11/2011 |
| WO | WO 2012/052565 A1 | 4/2012 |
| WO | WO 2013/087234 A1 | 6/2013 |

OTHER PUBLICATIONS

Dvir, T., et al.; Nano Letters, 2010, p. 250-254.*
Denard, B., et al.; eLife, 2012, p. 1-14.*
Jiang, J. et. al., "Toward photocontrolled release using light-dissociable block copolymer micelles." Macromolecules 39, 4633-4640 (2006).
Jiang, J. et. al., "A new design for light-breakable polymer micelles." Journal of the American Chemical Society 127, 8290-8291 (2005).
Babin, J. et al., "A new two-photon-sensitive block copolymer nanocarrier." Angew Chem Int Ed Engl 48, 3329-3332 (2009).
Fomina, N. et. al., "UV and near-IR triggered release from polymeric nanoparticles." Journal of American Chemical Society, vol. 132, No. 28, pp. 9540-9542 (2010).
Timko, B.P. et. al., "Remotely triggerable drug delivery systems." Advance Material vol. 22, No. 44, pp. 4925-4943 (2010).
Warrell, R.P, et. al., "Differentiation therapy of acute promyelocytic leukemia with tretinoin (all-trans-retinoic acid)." N Engl J Med 324, 1385-1393 (1991).
Russo, D. et al., "All-trans retinoic acid (ATRA) in patients with chronic myeloid leukemia in the chronic phase." Leukemia 12, 449-454 (1998).
Si, J. et. al., "CaMKII regulates retinoic acid receptor transcriptional activity and the differentiation of myeloid leukemia cells." . J Clin Invest 117, 1412-1421 (2007).
Boussif, O. et. al., "A versatile vector for gene and oligonucleotide transfer into cells in culture and in vivo: polyethylenimine." Proc Natl Acad Sci U S A 92, 7297-7301 (1995).

(Continued)

*Primary Examiner* — Robert Jones, Jr.
(74) *Attorney, Agent, or Firm* — Leason Ellis LLP

(57) ABSTRACT

The present subject matter relates to light-activatable polymeric nanoparticles (NPs) for the transportation and release of an active substance, methods for obtain said particles and their uses. A light-activatable nanoparticle for the transportation and release of an active substance, comprising a polycation preferably a polimer polycation, a polyanion and a light-sensitive photochrome attached to the polycation or the polyanion, wherein said photochrome is hydrophobic and suitable to photo-cleave when activated by an irradiation source, generating a negative charge and releasing the active substance. Light-activatable. The disclosure subject matter shows that NPs are a highly efficient drug delivery system to primary leukemic cells based on opto-nanomedicine system. Therefore, the present disclosure is useful for remote control in the release of biomolecules with spatio-temporal resolution with applications in the areas of general therapeutic and regenerative medicine applications.

20 Claims, 13 Drawing Sheets

(56) References Cited

OTHER PUBLICATIONS

Maia, J. et al.," Controlling the neuronal differentiation of stem cells by the intracellular delivery of retinoic acid-loaded nanoparticles." ACS Nano 5, 97-106 (2011).
Tiyaboonchai, W. et. al., "Formulation and characterization of amphotericin B-polyethylenimine-dextran sulfate nanoparticles." J Pharm Sci 90, 902-914 (2001).
Jose, J. et. al., "Syntheses and properties of water-soluble Nile Red derivatives." J Org Chem 71, 7835-7839 (2006).
Ruthardt, M., et al., "Opposite effects of the acute promyelocytic leukemia PML-retinoic acid recpetor alpha (RAR alpha) and PLZF-RAR alpha fusion proteins on retinoic acid signaling." Mol Cell Biol 17 (8), 4859-4869 (1997).
Dvir, T. et. al., "Photo-Targeted Nanoparticles." Nano Lett. vol. 10 No. (1): pp. 250-254. Jan. 2010.

* cited by examiner

SEQUENCE LISTING

```
<160> NUMBER OF SEQ ID NOS: 8

<210> SEQ ID NO 1
<211> LENGTH: 19
<212> TYPE: DNA
<213> ORGANISM: Homo sapiens
<220> FEATURE:
<221> NAME/KEY: source
<222> LOCATION: 1..19
<223> OTHER INFORMATION: /mol_type="unassigned DNA"
      /organism="Homo sapiens"

<400> SEQUENCE: 1
ccatcctcag aactcacaa                                                   19

<210> SEQ ID NO 2
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="unassigned DNA"
      /organism="Homo sapiens"

<400> SEQUENCE: 2
accagcgaga attaatacct                                                  20

<210> SEQ ID NO 3
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="unassigned DNA"
      /organism="Homo sapiens"

<400> SEQUENCE: 3
cacctagagg ataagcactt                                                  20

<210> SEQ ID NO 4
<211> LENGTH: 18
<212> TYPE: DNA
<213> ORGANISM: Homo sapiens
<220> FEATURE:
<221> NAME/KEY: source
<222> LOCATION: 1..18
<223> OTHER INFORMATION: /mol_type="unassigned DNA"
      /organism="Homo sapiens"

<400> SEQUENCE: 4
ggactcactg acagaaca                                                    18
```

```
<210> SEQ ID NO 5
<211> LENGTH: 18
<212> TYPE: DNA
<213> ORGANISM: Homo sapiens
<220> FEATURE:
<221> NAME/KEY: source
<222> LOCATION: 1..18
<223> OTHER INFORMATION: /mol_type="unassigned DNA"
      /organism="Homo sapiens"

<400> SEQUENCE: 5
ccaccttctt gctcctac                                                 18

<210> SEQ ID NO 6
<211> LENGTH: 18
<212> TYPE: DNA
<213> ORGANISM: Homo sapiens
<220> FEATURE:
<221> NAME/KEY: source
<222> LOCATION: 1..18
<223> OTHER INFORMATION: /mol_type="unassigned DNA"
      /organism="Homo sapiens"

<400> SEQUENCE: 6
ctttcaccct ctgttcct                                                 18

<210> SEQ ID NO 7
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="unassigned DNA"
      /organism="Homo sapiens"

<400> SEQUENCE: 7
agccacatcg ctcagacacc                                               20

<210> SEQ ID NO 8
<211> LENGTH: 19
<212> TYPE: DNA
<213> ORGANISM: Homo sapiens
<220> FEATURE:
<221> NAME/KEY: source
<222> LOCATION: 1..19
<223> OTHER INFORMATION: /mol_type="unassigned DNA"
      /organism="Homo sapiens"

<400> SEQUENCE: 8
gtactcagcg ccagcatcg                                                19
```

LIGHT-ACTIVATABLE POLYMERIC NANOPARTICLES

CROSS-REFERENCE TO RELATED APPLICATIONS

This application is a U.S. National Stage Application under 35 U.S.C. §371 of International Patent Application No. PCT/IB2014/064399, filed Sep. 10, 2014 which claims priority to Portugal Patent Application No. 107150, filed Sep. 10, 2013, which are hereby incorporated by reference as if set forth in their respective entireties herein.

TECHNICAL FIELD

The present subject matters relates to light-activatable polymeric nanoparticles (NPs) for the transportation and release of an active substance, methods for obtain said particles and their uses.

BACKGROUND ART

The development of triggerable systems that allow precise control of the timing, duration and magnitude of drug release is important for therapeutic medicine. Micellar aggregates (core-shell micelles, vesicles, etc.) formed by amphiphilic block copolymers or small molecule surfactants have been reported as possible light-activatable drug delivery systems (Jiang, J., Tong, X., Morris, D. & Zhao, Y. Toward photo-controlled release using light-dissociable block copolymer micelles. Macromolecules 39 (2006); Jiang, J., Tong, X. & Zhao, Y. A new design for light-breakable polymer micelles. Journal of the American Chemical Society 127 (2005)). In this sense, polymer micelles could release the drugs at a required time and tumor location. In some cases the dissociation of the micelles occurs due to structural arrangements of the photo-sensitive molecule attached to the block copolymer or surfactant. In other cases, the interaction of the photo-sensitive molecule with light results in a structural change that alters the hydrophilic/hydrophobic balance toward the disassembly of the micelle (Babin, J. et al. A new two-photon-sensitive block copolymer nanocarrier. Angew Chem Int Ed Engl 48, 3329-3332 (2009)). Recently, these studies have been extended to NPs that disassemble in reaction to light (Fomina, N., McFearin, C., Sermsakdi, M., Edigin, O. & Almutairi, A. UV and near-IR triggered release from polymeric nanoparticles. J Am Chem Soc 132, 9540-9542 (2010); Timko, B. P., Dvir, T. & Kohane, D. S. Remotely triggerable drug delivery systems. Adv Mater 22, 4925-4943 (2010)). However, the demonstration that these systems can be used to release efficiently biomolecules within cells either in vitro or in vivo with precise temporal and dosage control remains elusive. These systems should be formed by (i) components that can be eliminated by the human body while being able to (ii) efficiently cross the cell membrane and (iii) disassemble by light releasing consequently the cargo.

Additionally, retinoic acid (RA) as a differentiation agent is used in the clinic for the treatment of human chronic myelogenous leukemia (CML), human acute promyelocytic leukemia (APL) and acute myeloid leukemia (AML) (Warrell, R. P., Jr. et al. Differentiation therapy of acute promyelocytic leukemia with tretinoin (all-trans-retinoic acid). N Engl J Med 324, 1385-1393 (1991); Russo, D. et al. All-trans retinoic acid (ATRA) in patients with chronic myeloid leukemia in the chronic phase. Leukemia 12, 449-454 (1998)). RA activates nuclear RA receptors (RARs) that forms heterodimers with retinoid X receptors (RXRs) which in turn binds to the RA response element (RARE) resulting in the activation of target genes causing cell growth arrest, apoptosis and differentiation (Si, J., Mueller, L. & Collins, S. J. CaMKII regulates retinoic acid receptor transcriptional activity and the differentiation of myeloid leukemia cells. J Clin Invest 117, 1412-1421 (2007). However, in some cases, the intracellular concentration of RA available is relatively low to induce significantly the differentiation of leukemia cells, due to the low solubility of RA in physiologic milieu and low capacity to accumulate in cell cytoplasm.

So, in order to overcome the problems of the state of the art, the present invention and different embodiments established an opto-nanomedicine approach for the treatment and study of leukemic (stem) cells either in vitro or in vivo. This new technology allows remote control in the release of biomolecules with spatio-temporal resolution. The light-activatable NPs disclosed are suitable for general therapeutic and regenerative medicine applications.

The NP formulation described here is irreversible disassembled by a photochemical process (UV or blue laser). Several light-activatable polymeric NPs have been reported[12], however the internalization and intracellular trafficking of these NPs containing bioactive agents and their effect in the modulation/differentiation of cells both in vitro and in vivo has not been studied. Here, we demonstrate the precise spatial and temporal control in the release of RA. We show for the first time that cells transfected with light-activatable NPs can be activated after 2 days while maintaining the same inductive properties. This gives an opportunity to use cells as "Trojan horses" for activation at specific sites of human body.

Although several NP formulations have been reported for the release of RA, including from our group, no formulation can release high doses of RA (120 µg of RA per mg of NP) in minutes-range. This is very important to enhance the differentiation of leukemic cells, in particular in APL caused by PLZF/RARα, which exhibits impaired sensitivity to RA. In this case, the light-activated RA$^+$NPs enhanced 2-4 fold the differentiation of the leukemic cells as compared to cells treated with non-activated RA$^+$NPs.

These facts are disclosed in order to illustrate the technical problem addressed by the present disclosure.

SUMMARY OF THE DISCLOSURE

The disclosure subject matter relates to a light-activatable nanoparticle for the transportation and release of an active substance, comprising a polycation, namely a polimer polycation, a polyanion and a light-sensitive photochrome attached to the polycation or the polyanion, wherein said photochrome is hydrophobic and suitable to photo-cleave when activated by an irradiation source, generating a negative charge and releasing the active substance.

In an embodiment of the light-activatable nanoparticle disclosed the said polycationic polymer is at least one of the followings: poly(ethyleneimine), polylysine, poly(amino esters), poly(disulfide amines), chytosan, or others that one skilled in the art will recognize.

In other preferred embodiment the said light-sensitive photochrome is at least one of the followings: an o-nitrobenzyl (o-NB) alcohol derivative, coumarin, 4,5-dimethoxy-2-nitrobenzyl chloroformate or others that someone skilled in the art will recognize.

In other embodiment of the light-activatable nanoparticle disclosed the polyanion is at least one of the followings: dextran sulphate, polyaspartic acid, hyaluronic acid, among others.

In other embodiment the light-activatable nanoparticle comprises: poly(ethyleneimine) (PEI) as polycation; 4,5-dimethoxy-2-nitrobenzyl chloroformate (DMNC) as a light-sensitive photochrome and dextran sulphate as polyanion.

In another embodiment of the light-activatable nanoparticle disclosed the said active substance may be at least one of the followings: a cellular modulation agent, including a differentiating agent, a metabolic regulator, a cell cycle regulator, an epigenetic regulator, a reprogramming agent, a transcription factor, among others; in particular retinoic acid.

In another embodiment of the light-activatable nanoparticle disclosed the molar ratio of DMNC to PEI could be between 1% and 100%.

In another embodiment of the light-activatable nanoparticle disclosed the final degree of substitutions PEI-DMNC can be between 20-100%, preferably 25-50%.

In another embodiment of the light-activatable nanoparticle disclosed the average diameter of the nanoparticle may be between 1-1000 nm, preferably 100-300 nm, more preferably 160 nm.

In another embodiment of the light-activatable nanoparticle disclosed said irradiation source may be UV light or a blue laser, among others.

In another embodiment the light-activatable nanoparticle disclosed can be for use in medicine, namely in regenerative medicine preferably for use in the treatment of neoplasias or cancer diseases, more preferably, for use in the treatment of leukemia.

The light-activatable nanoparticle disclosed are able to transfer stem cells, allowing their homing into the in vivo niche (for example bone marrow) and then activating the said nanoparticles remotely by a laser.

Another aspect of the present subject matter also discloses a composition comprising the light-activatable nanoparticle disclosed. Preferably, a pharmaceutical, a medical or a cosmetic composition.

In another embodiment the light-activatable nanoparticle formulation may comprise a concentration of said nanoparticles up to 100 µg/mL.

In another embodiment of the said composition light-activatable nanoparticle disclosed may be a topic formulation or an injectable formulation.

In another embodiment of the light-activatable, to improve the stabilization of NP formulation zinc sulfate may be added.

Another aspect of the present subject matter also discloses a method for obtaining light-activatable polymeric nanoparticles comprising the following steps:
  derivatizing the polycation with the photochrome in DMSO;
  precipitation of polycation-photochrome solution into an aqueous solution of a polyanion,
  separation of the nanoparticles from the remaining polymers, preferably by centrifugation or dialysis.

In another embodiment the method for obtaining light-activatable polymeric nanoparticles comprises the following steps:
  Derivatizing the poly(ethyleneimine) with 4,5-dimethoxy-2-nitrobenzyl chloroformate in DMSO, in presence of triethylamine;
  precipitation of PEI-DMNC solution into an aqueous solution of dextran sulphate, the polyanion.

In another embodiment zinc sulfate may be added as stabilizer to obtain a more stable light-activatable polymeric nanoparticles.

The present disclosure shows that light-activatable polymeric NPs may enhance the efficiency of transportation and release of an active substance to the target cells, in particular RA delivery to leukemic cells either in vitro or in vivo. The light-activatable polymeric NPs disclosed in the present subject matter surprisingly allow that the timing of drug release following delivery by NPs can be tightly controlled, in particular the efficiency of differentiation of leukemic cells induced by RA can be increased. The efficiency is due to a combination of several factors including (i) high internalization in terms of kinetics (in the first 4-6 h) and in magnitude (60 and 75 pg of NPs per cell following exposure for 4 h to cell culture medium containing 100 µg/mL of NPs), (ii) high endolysosomal escape (80% of the NPs escape the endolysosomal compartment in the first 2 h; this is approximately 18 pg of NPs per cell), (iii) durable intracellular accumulation of the NPs (no exocytosis mediated by Pgp; accumulation for more than 5 days in $CD34^+$ cells) and (iv) fast disassembly of the NPs once activated by UV or blue light (minutes range).

The present disclosure also shows that is possible to activate light-activatable NPs that have been accumulated in the cell cytoplasm for a few days (at least 48 h) and trigger the release of their payload.

BRIEF DESCRIPTION OF THE DRAWINGS

The following figures provide preferred embodiments for illustrating the description and should not be seen as limiting the scope of invention. The figures that do not fall under the scope of the claims represent reference examples.

DETAILED DESCRIPTION

The development of a nanoparticle system possessing a trigger to allow precise control of the timing, duration and magnitude of drug release is important for therapeutic and regenerative medicine, namely in cancer chemotherapy. A light-activatable polymeric nanoparticles (NPs) that rapidly release an active substance namely, retinoic acid (RA), when exposed to a blue laser/UV light is disclosed. These NPs reduce the clonogenicity of bone marrow tumor cells from patients with acute myeloid leukemia (AML) and induce the differentiation of RA-low sensitive leukemia cells expressing the chimeric promyelocytic leukemia zinc finger/RARα (PLZF/RARα) fusion protein.

In another embodiment, RA released from light-activated NPs was superior at inducing leukemia cell differentiation compared to RA released by passive diffusion. Further, we demonstrate the importance of temporal activation of the nanoformulation during the intracellular trafficking to maximize RA effect and show in vivo that leukemic cells loaded with NPs can be light-activated to release RA, thereby allowing greater spatio-temporal control of drug delivery.

NPs can enhance the efficiency an active substance, namely RA delivery to leukemic cells either in vitro or in vivo. We further show that the timing of drug release following delivery by NPs can be tightly controlled, and that the efficiency of differentiation of leukemic cells induced by RA can be increased.

Figure 7:
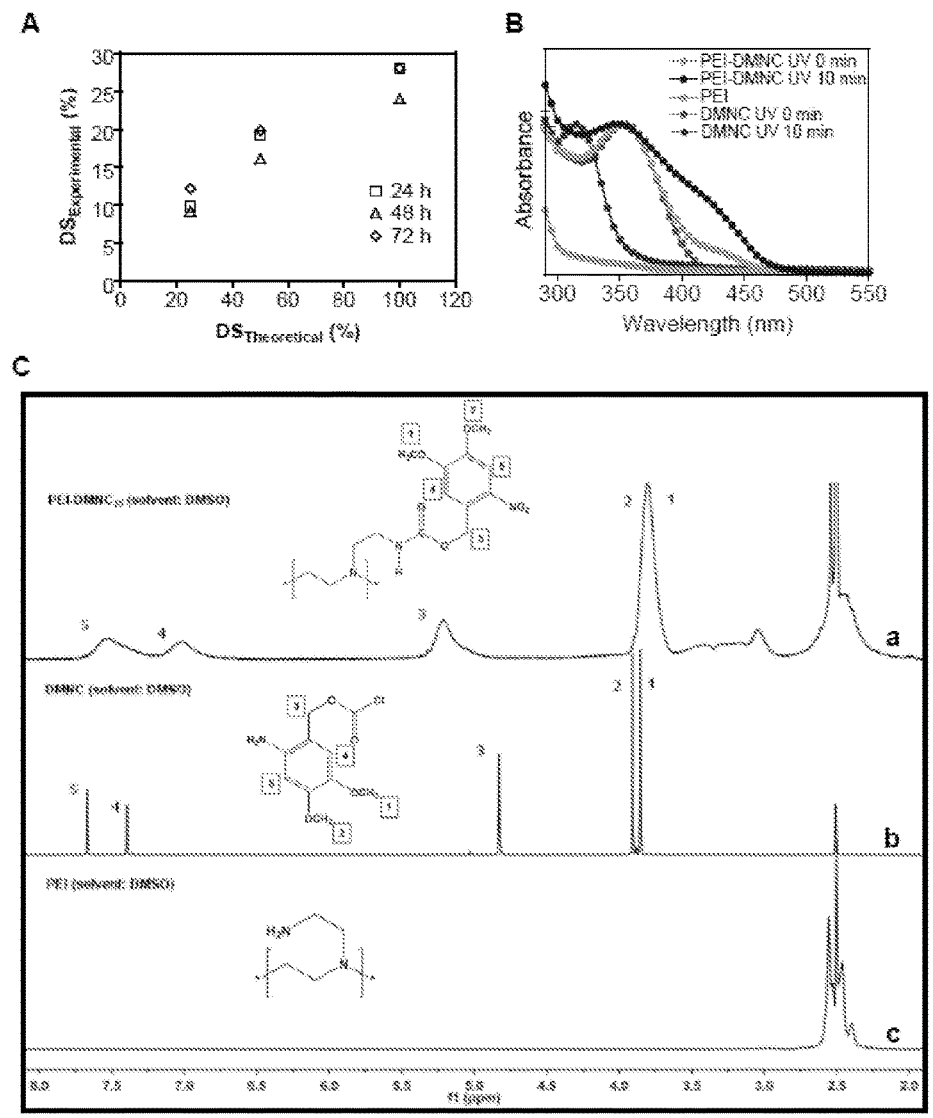
FIG. 7: Characterization of PEI derivatized with DMNC. (A) Degree of substitution (DSn) of PEI with DMNC. The DStheoretical was calculated as molar ratio of DMNC to tertiary amines in PEI. The DSexperimental was determined by spectrophotometry. (B) Effect of 10 min-UV exposure (365 nm, 100 Watts) in the absorbance of DMNC (250 μg/mL, in DMSO), PEI (1 mg/mL, in DMSO), and PEI-DMNC25 (1 mg/mL, in DMSO) conjugate. For DMNC, the absorption maximum at 355 nm reverted to baseline levels after 10 min of UV exposure, indicating the photo-cleavage of DMNC, and a new absorption peak was observed at 320 nm, due to the formation of 4,5-dimethoxy-2-nitrobenzyl alcohol (DMNA). For PEI-DMNC, there was a decrease in the intensity of the peak at 355 nm and a concomitant increase in the peak at 320 nm; however our results suggest that not all the attached DMNC molecules were photo-cleaved. (C) 1H NMR spectra of PEI, DMNC and PEI-DMNC. 1H NMR spectra of (a) PEI-DMNC conjugate in DMSO-d6, (b) DMNC in DMSO-d6 and (c) PEI in DMSO-d6, showing effective conjugation between PEI and DMNC.

To prepare an embodiment of the present invention light-dissociable polymeric NPs, poly(ethyleneimine) (PEI, Mw of 25 kDa) was initially derivatized with 4,5-dimethoxy-2-nitrobenzyl chloroformate (DMNC) in DMSO, a light-sensitive photochrome (FIG. 1A). PEI was selected as initial NP block because it facilitates the cellular internalization of NPs and subsequent escape from endosomes (Boussif, O. et al. A versatile vector for gene and oligonucleotide transfer into cells in culture and in vivo: polyethylenimine. Proc Natl Acad Sci USA 92, 7297-7301 (1995); Maia, J. et al. Controlling the neuronal differentiation of stem cells by the intracellular delivery of retinoic acid-loaded nanoparticles). ACS Nano 5, 97-106 (2011)), while DMNC was selected because responds rapidly to light and the degradation products are relatively non-cytotoxic (Dvir, T., Banghart, M. R., Timko, B. P., Langer, R. & Kohane, D. S. Photo-targeted nanoparticles. Nano Lett 10, 250-254 (2010)). Synthesis of PEI-DMNC conjugates with different degree of substitution (PEI-DMNC100; PEI-DMNC50 and PEI-DMNC25 with a theoretical degree of substitution of 100%, 50% and 25% of the tertiary amines of PEI) were performed in the presence of triethylamine for 24 h, at 25° C. The conjugation of DMNC to PEI was confirmed by spectrophotometry (FIG. 7A) and $^1$H-NMR (FIG. 7C). Approximately 20% of the initial DMNC added to the reaction vial reacted with PEI. Moreover, the final degree of substitution in PEI-DMNC was controlled by varying the molar ratio of DMNC to PEI (FIG. 7A). To prepare NPs, a solution of PEI-DMNC in DMSO was precipitated into an aqueous solution of dextran sulfate. NPs were formed because of the hydrophobicity of PEI-DMNC conjugate and the electrostatic interaction of PEI-DMNC (polycation) with dextran sulfate (DS, polyanion). To stabilize the NP formulation, zinc sulfate was added. NPs with a diameter between 150 (PEI-DMNC$_{100}$:DS NP) and 110 nm (PEI-DMNC$_{25}$:DS NP) and a zeta potential between 20 (PEI-DMNC$_{100}$:DS NP) and 25 mV (PEI-DMNC$_{25}$:DS NP) were prepared.

To verify that DMNC could be photo-degraded, solutions of DMNC or PEI-DMNC in DMSO were exposed to UV-light (365 nm, 100 Watts) for 10 min and then analyzed by spectrophotometry. For DMNC, the absorption maximum at 355 nm reverted to baseline levels after 10 min of UV exposure, indicating the photo-cleavage of DMNC, and a new absorption peak was observed at 320 nm, due to the formation of 4,5-dimethoxy-2-nitrobenzyl alcohol (DMNA) (FIG. 7B). For PEI-DMNC, there was a decrease in the intensity of the peak at 355 nm and a concomitant increase in the peak at 320 nm; however the results suggest that not all the attached DMNC molecules were photo-cleaved (FIG. 7B). NMR results suggest that PEI is retarding the photo-cleavage of the attached DMNC (FIG. 7C).

In an embodiment of the present invention to prepare NPs, a solution of PEI-DMNC (50 mg/mL, in DMSO) was precipitated into an aqueous solution of dextran sulfate (2 mg/mL). NPs were formed because of the hydrophobicity of PEI-DMNC conjugate and the electrostatic interaction of PEI-DMNC (polycation) with dextran sulfate (DS, polyanion). To improve the stabilization the NP formulation, zinc sulfate may be added (Maia, J. et al. Controlling the neuronal differentiation of stem cells by the intracellular delivery of retinoic acid-loaded nanoparticles. ACS Nano 5, 97-106 (2011); Tiyaboonchai, W., Woiszwillo, J. & Middaugh, C. R. Formulation and characterization of amphotericin B-polyethylenimine-dextran sulfate nanoparticles. J Pharm Sci 90, 902-914 (2001)). In another embodiment the NPs with a diameter between 150 (PEI-DMNC$_{100}$:DS NP) and 110 nm (PEI-DMNC$_{25}$:DS NP) and a zeta potential between 20 (PEI-DMNC$_{100}$:DS NP) and 25 mV (PEI-DMNC$_{25}$:DS NP) were formed.

To demonstrate that PEI-DMNC:DS NP formulation could be photo-disassembled, a suspension of NPs (50 μg/mL) was exposed to UV light for up to 10 min and both the diameter, counts per second (i.e., number of NPs per volume unit) and zeta potential were assessed. The number of NPs decreased below half of the initial number after 1 min of UV exposure indicating NP disassembly (FIG. 1B). Under UV irradiation, the photolysis of DMNC disrupts the NPs because of the changing of hydrophilic-hydrophobic balance in the NP. In addition, the NPs that remained in suspension had a significant decrease in diameter from 110 to 5 nm after 10 min of UV exposure, while zeta potential was kept constant (25 mV). Importantly, UV light can be replaced by a blue laser (404 nm, 80 mW), which has minimal impact in cell biology, to induce the photo-disassembly of PEI-DMNC:DS NPs. As observed for UV-exposed NPs, blue light-exposed NPs have a decrease in number and in diameter overtime (FIG. 8D).

Figure 8:
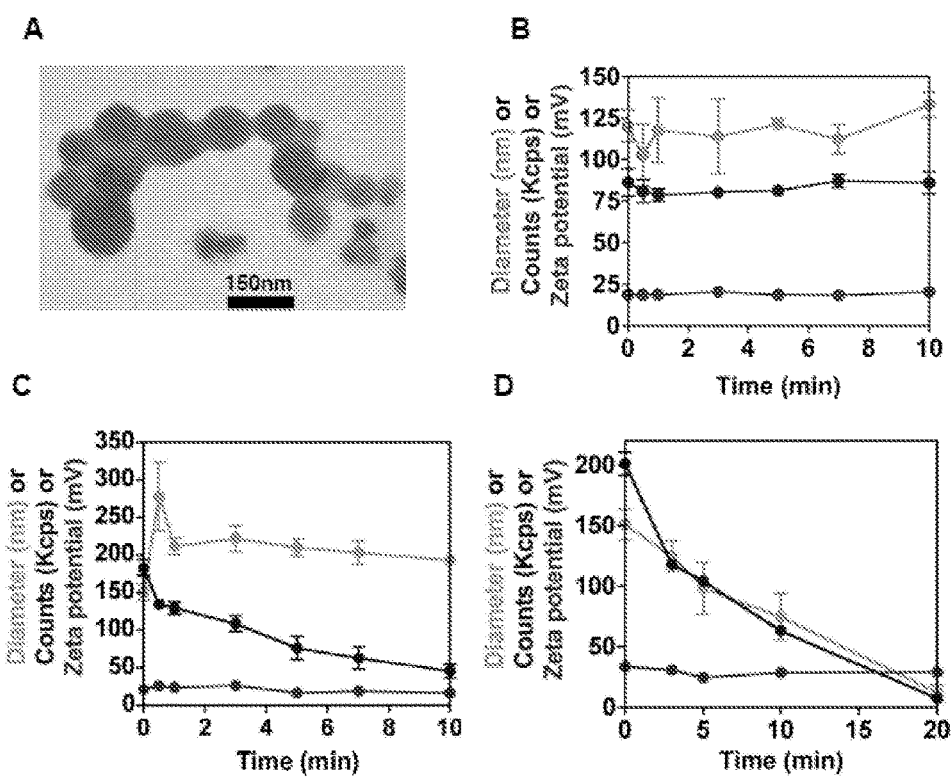
FIG. 8: Light-activation of NPs. (A) SEM of PEI-DMNC25:DS NPs. (B,C,D) Blue laser (405 nm, 80 mW) activation of PEI:DS NPs (B), PEI-DMNC100:DS (C) and PEIDMNC25: DS NPs (D). A suspension of NPs (n=3) (100 μL, 100 μg, in water) was exposed to a blue laser up to 20 min. Then, the NP suspension was diluted up to 50 μg/mL in water and the size, zeta potential and number of NPs (Kcps) in the suspension was evaluated by dynamic light scattering.
Figure 9:
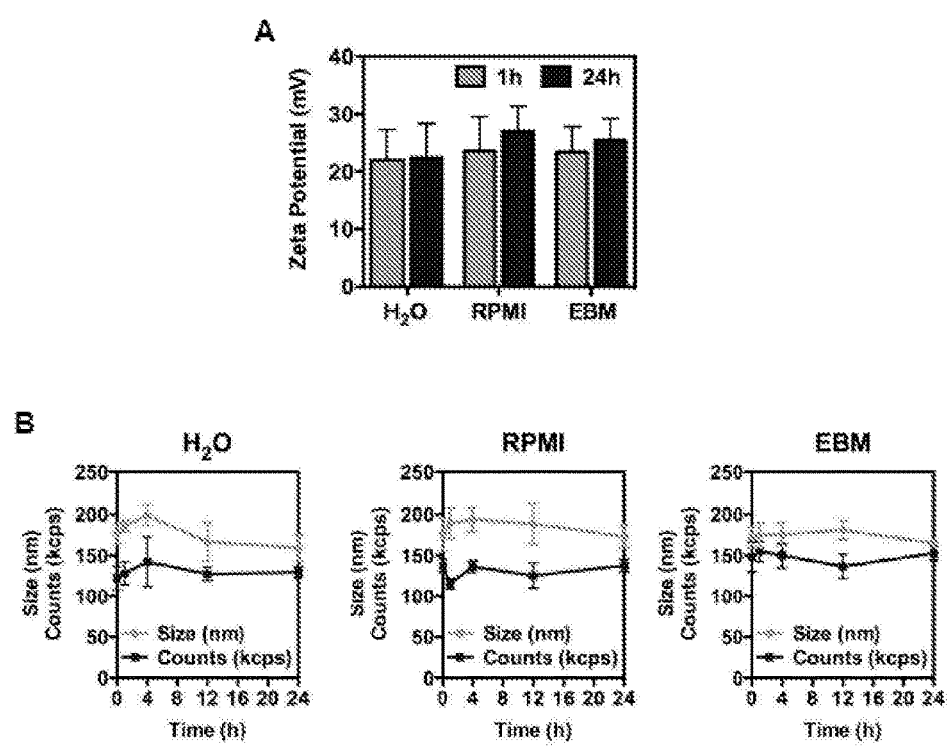
FIG. 9: Stability of NPs suspended in basal culture medium. (A) Zeta potential of NPs suspended in H2O, basal RPMI medium or EBM medium. (B) Diameter (nm) and counts (Kcps) of NPs suspended in H2O, basal RPMI medium or EBM medium. A suspension of NPs (2 mL, 25 μg/mL) was prepared and diameter, counts and zeta potential determined by dynamic light scattering method (DLS) using a Zeta Plus Analyzer (Brookhaven). Results are expressed as Mean±SEM (n=3).
Figure 10:
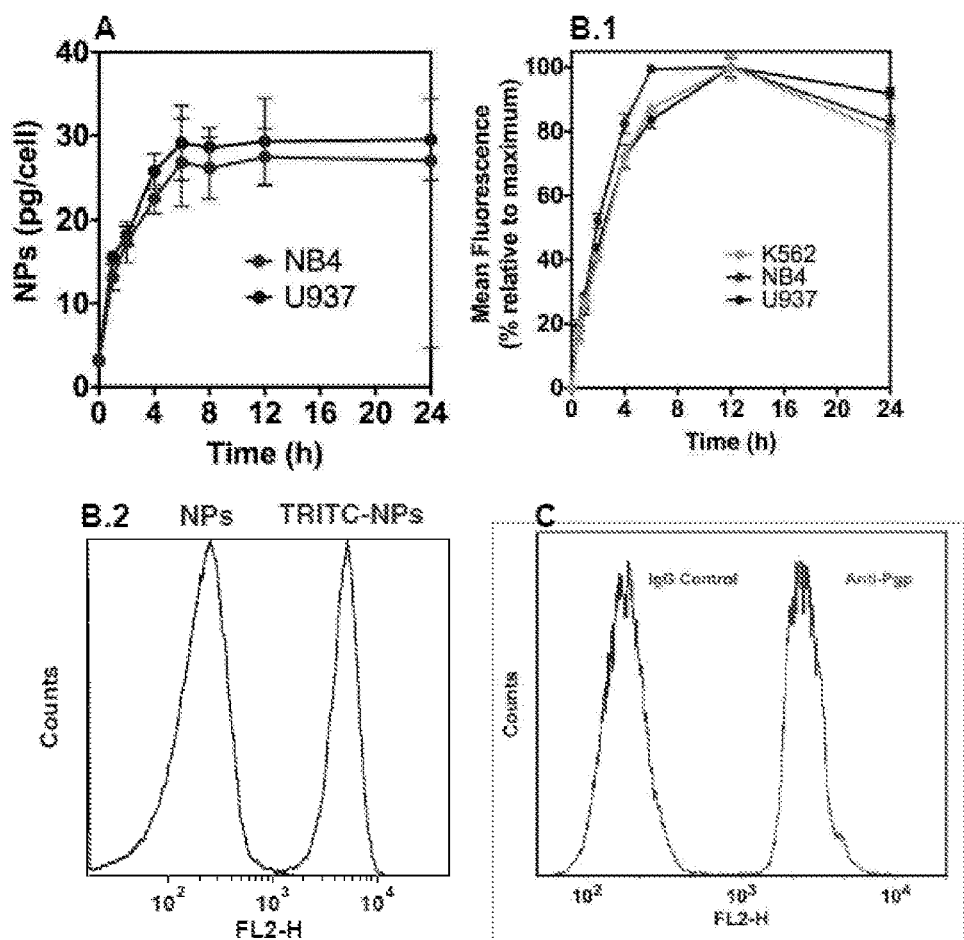
FIG. 10: Cellular uptake of NPs. (A) Quantification of NP internalization in leukemia cell lines NB4 and U937 as determined by ICP-MS analysis (Zn quantification). Cells were incubated with 10 μg/mL NPs up to 24 h. After each incubation period, the cells were extensively washed with PBS followed by the addition of an aqueous solution of nitric acid (1 mL, 69% (v/v)). The concentration of intracellular levels of Zn was quantified by ICP-MS. The concentration was normalised per cell. The estimation of NPs was done based on standard solutions. The results are expressed as Mean±SEM (n=3). (B.1) Uptake of TRITC-labeled NPs in leukemia cells as determined by FACS. Cells were cultured in medium supplemented with NPs for the time specified in the graph, washed and characterised by FACS. The results are expressed as Mean±SEM (n=3). (B.2) AML stem cells (CD34+CD38−) were labeled with TRITC-labeled NPs for 4 h and then cultured for 5 days. The histogram plot shows the percentage of cells labelled after 5 days. (C) Expression of Pgp in U937 cells as evaluated by FACS. A PE-conjugated mouse anti-human P-glycoprotein has been used (Abcamab93590—Clone UIC2).
Figure 11:
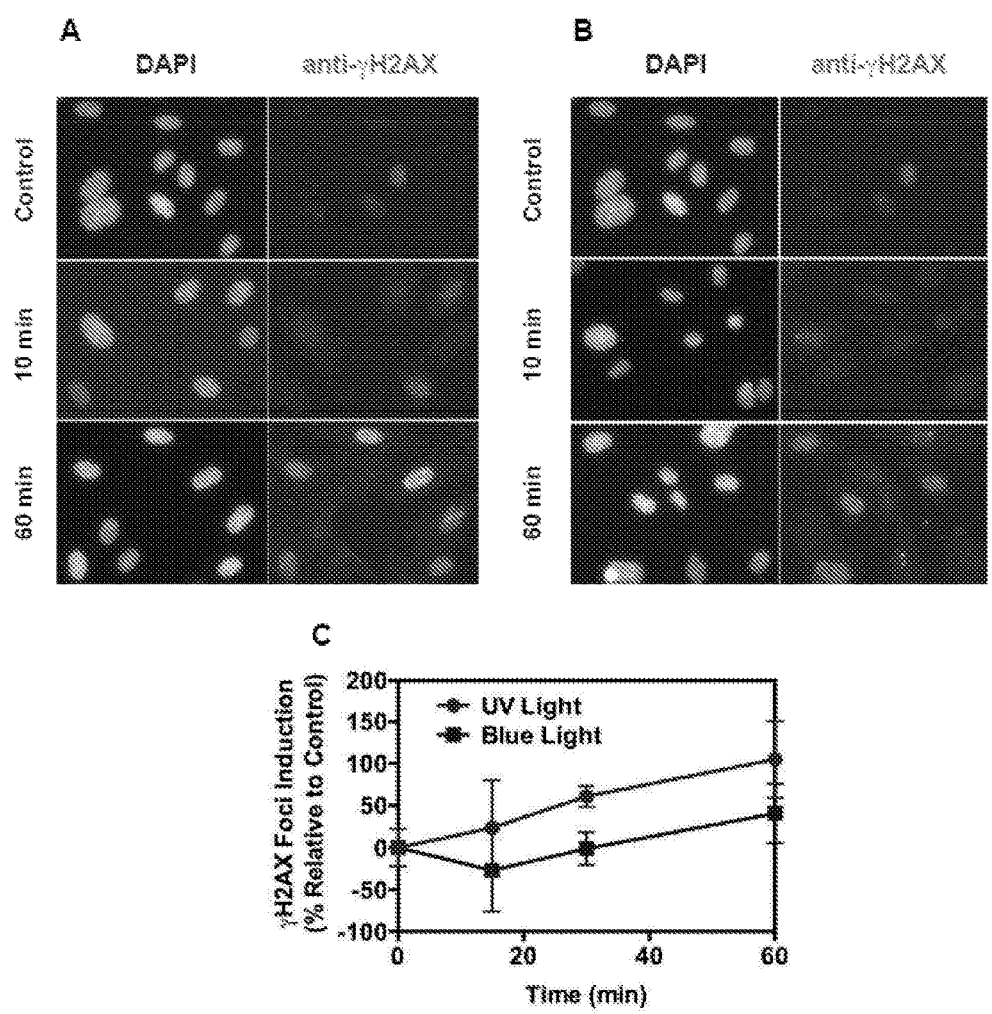
FIG. 11: Effect of UV light and Blue Light in DNA damage in HUVEC cells. Immunofluorescent staining of normal HUVEC cells mock treated or exposed to 10 min or 60 min of UV light (365 nm, 100 W) (A) or blue light (405 nm, 80 mW) (B) and allowed to recover for 6 h. Cells were then fixed and stained to readily identify γH2AX-containing foci, as biomarker for nuclear sites of DNA damage in affected cells. (C) Time-dependent increase of γH2AX after UV light (365 nm, 100 W) or blue light (405 nm, 80 mW) irradiation. Quantitative analysis of foci intensity were quantified using image) software and normalised to the control condition.

The response of the NPs to UV light was mediated by DMNC coupled to one of the components of the NP, since NPs without DMNC did not respond to light (FIGS. 8A and 9A). In addition, the concentration of DMNC conjugated to PEI is important for the light-responsiveness of the NP. NPs formed by PEI with high degree of substitution with DMNC are less susceptible to photo-disassembly than NPs with PEI with low degree of substitution (FIG. 8C). Therefore, for subsequent studies the NP formulation having PEI with low degree of substitution was selected (PEI-DMNC$_{25}$:DS NP). To further confirm light-disassembly of the NPs, the NPs were conjugated with quantum dots (Qdots525) and their fluorescence monitored overtime after exposure of small regions of the NP to a blue confocal laser (405 nm). The results show that fluorescence intensity increases after light exposure due to the disassembly of the NP and the decrease in the quenching of Qdot fluorescence after NP disassembly (FIG. 1D).

To evaluate the characteristics of light-activatable polymeric NPs as a controlled release system, NPs were encapsulated with Niles Red (NR), a small hydrophobic dye with excellent photostability. NR fluorescence at about 530 nm shows good quantum yields in apolar solvents. When exposed to water its fluorescence emission shows a shift to approximately 640 nm and the quantum yield is significantly reduced (Jose, J. & Burgess, K. Syntheses and properties of water-soluble Nile Red derivatives. J Org Chem 71, 7835-7839 (2006)). The NP suspension was then exposed to UV light for up to 10 min and NP properties (diameter, counts, zeta potential) as well as release of NR were evaluated. As obtained for blank NPs, the number of NR containing NPs decreased overtime, indicating the encapsulated NR did not affect the photo-cleavage of the NPs (FIG. 1C). Then, the release of NR upon UV exposure was monitored by fluorescence spectroscopy (FIG. 1E). The fluorescence intensity (in percentage) of the NP suspension decreased to 20% of the initial value after 10 min of UV exposure, due to the controlled triggered burst release of NR in aqueous solution. In contrast, no significant release of NR was observed for NPs not exposed to UV light.

Induction of leukemic cell differentiation by RA is a therapeutic strategy that has been used with great success in the treatment of acute promyelocytic leukaemia (APL). APL is a subtype of acute myeloid leukaemia (AML) characterized by a unique translocation between chromosomes 15 and 17, which leads to the formation of the fusion oncogene PML-RARα involving the transcription factor RA receptor alpha (RARα). RA activates nuclear RA receptors (RARs) that forms heterodimers with retinoid X receptors (RXRs) which in turn binds to the RA response element (RARE) resulting in the activation of target genes causing cell growth arrest, apoptosis and differentiation. Despite its clear therapeutic efficacy, approximately 25% of patients receiving RA will develop serious complications including the "differentiation syndrome". Clinical trials of RA in other types of AML have been less successful, possibly because of the relatively higher concentrations of RA that are required to induce differentiation in non-APL AML. For both of these reasons, the design of a delivery system with precise temporal and dosage control will be important for leukemia treatment.

The present disclosure surprisingly show that light-activatable polymeric NPs can enhance the efficiency of RA delivery to leukemic cells either in vitro or in vivo. We further show that the timing of drug release following delivery by NPs can be tightly controlled, and that the efficiency of differentiation of leukemic cells induced by RA can be increased.

NPs have no substantial effect in cell metabolism of human leukemic cells such as chronic myelogenous leukemia (CML) K562 cells, human bone marrow acute promyelocytic leukemia (APL) NB4 cells and human myelomonoblastic cell line U937, as evaluated by an ATP assay, for concentrations up to 100 µg/mL. Cells were exposed to NPs for 4 h, washed to remove NPs not taken up by the cells, either exposed or not to UV light for 10 min, and finally cultured for additional 20 h (FIG. 2B).

Figure 12:
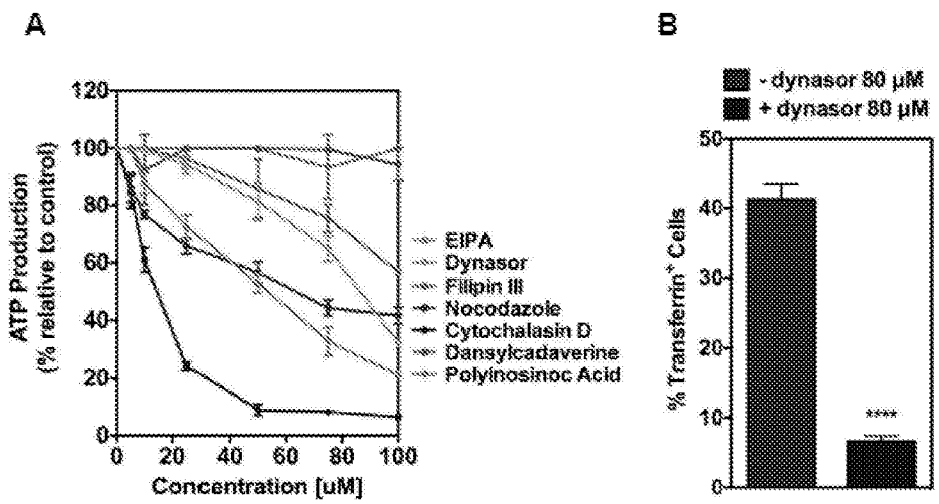
FIG. 12: (A) Cytotoxicity of chemical inhibitors against U937 cells. Cells were cultures in medium supplemented with growing concentrations of chemical inhibitors for 24 h. Cell cytotoxicity was evaluated by an ATP kit. Results are expressed as Mean±SEM (n=3). (B) Transport of FITC-labeled transferrin (1 μg/mL) known to selectively enter cells via clathrin-mediated endocytosis. Dynasor at concentration of 80 μM inhibits the internalisation of transferrin in U937 cells. Cells were exposed to culture medium with and without dynasor for 30 min, exposed to FITC-labeled transferrin for 3 min, at 4° C., and finally characterized by FACS. Results are expressed as Mean±SEM (n=3). **** Denotes statistical significance (P<0.0001).
Figure 13:
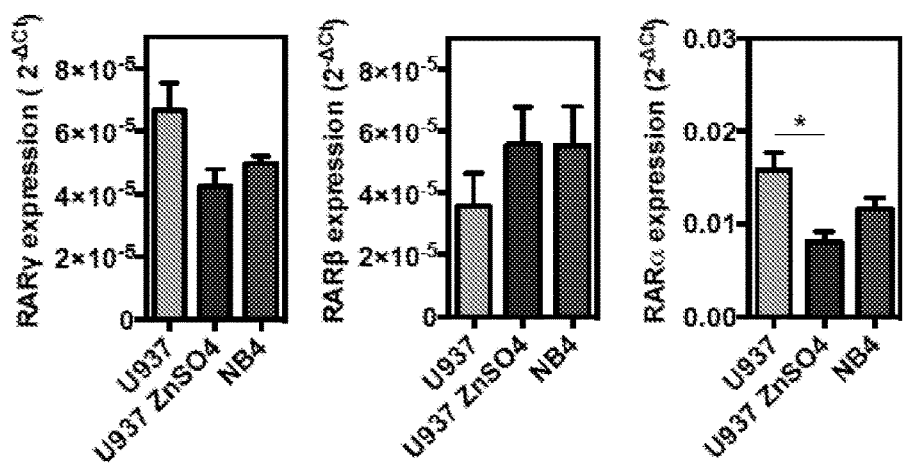
FIG. 13: Expression of RAR-α, RAR-β and RAR-γ genes (normalized to GAPDH) in human leukemia cell lines as assessed by qRT-PCR analysis. Results are expressed as Mean±SEM (n=3).

To identify the pathways of NP internalization, U937 cells were incubated in the presence of endocytosis chemical inhibitors at concentrations that were not cytotoxic for the cells (FIG. 12A), after which, fluorescently labelled NPs were added and the internalization monitored by flow cytometry. Filipin III inhibits cholesterol dependent internalization mechanisms, ethylisopropylamiloride (EIPA) inhibits macropinocytosis, nocodazole inhibits microtubule dependent pathways, cytochalasin D inhibits all pathways dependent on actin (including macropinocytosis), dansylcadaverine and dynasore inhibits clathrin-mediated endocytosis and polyinosinic acid inhibits scavenger receptors. Whenever possible molecules that enter by a specific internalization pathway were used as positive controls to show the efficacy of our inhibitors (FIG. 12B). Dynasore treatment (clathrin-mediated endocytosis (CME) inhibitor) reduced the uptake of NPs by 90%, compared to control cells (FIG. 2C.1). To confirm the endocytosis mechanisms involved in NP internalization, U937 cells were transfected with siRNAs to down-regulate key components of different endocytic mechanisms (FIG. 2C.2). We observed a ~60% and ~70% reduction on NPs uptake upon downregulation of clathrin heavy chain (CLTC), and low-density lipoprotein receptor (LDLR), respectively, confirming a role for CME. The knockdown of macropinocytosis regulators (Rac1 and CTBP1), led to a ~40% and ~50% decrease in NPs uptake, suggesting that macropinocytosis was also involved in NPs internalization. Downregulation of Caveolin 1 (CAV1), involved in caveolin-mediated endocytosis, and GPI-anchored protein-enriched early endocytic compartment/clathrin-independent carriers (GEEC-CLIC) pathways (CDC42) had no significant impact in NPs uptake. To further elucidate the intracellular trafficking of the NPs, we used adherent cells (HUVECs) to facilitate the characterization by confocal microscopy. The intracellular trafficking of the NPs was assessed first by performing a LysoTracker staining to see the general distribution of the FITC-labeled NPs in the endolysosomal system (FIG. 2D). During the first few hours of incubation with FITC-labeled NPs there was a clear drop in the intensity of LysoTracker in the cell suggesting a decrease in the pH of the endosomal vesicles by the presence of PEI (a strong base) in the cell and also possible vesicle disruption as the FITC-labeled NPs signal was increased in the cytoplasm. At later time points (12 hours) of incubation with FITC-labeled NPs the intensity of LysoTracker reached control levels suggesting that the endolysosomal system regained its normal characteristics (FIG. 2D). To fully characterize the route of FITC-labeled NPs inside the endolysosomal system a time-dependent colocalization study of FITC-labeled NPs with the specific markers: EEA1 for early endosomes, Rab-5 for early/late endosomes and Rab-7 for late endosome/lysosomes was done. For short incubation times (1-2 h) not many vesicles are seen with FITC-labeled NPs; instead there is a diffuse distribution of green allover the cytoplasm (ca. 80-90% of the fluorescence). This is consistent with a rapid escape of the NPs from endosomes after entering the cell likely due to their buffering capacity, leading to osmotic swelling and rupture of endosomes[14]. For later time points (over 5 hours) of incubation with FITC-labeled NPs there is a clear accumulation of FITC-labeled NPs inside vesicles that are mostly Rab-5 and/or Rab-7 positive with very low EEA-1 colocalization. The high colocalization with Rab-5 and the size of the vesicles containing NPs suggests that macropinocytosis is also an entrance route for these NPs (FIG. 2E). Taken together, our results indicate that the major endocytic mechanism for the internalization of the NPs is clathrin-mediated endocytosis. Our siRNA results indicate that macropinocytosis might be also involved but at minor extent. It is likely that both endocytic pathways are interconnected as demonstrated recently for lipid nanoparticles. Our results further show that the internalization of the NPs is rapid and in the first 2 h a significant percentage of NPs tend to escape the endolysosomal compartment, while the ones that did not escape accumulate in early/late endosomes.

Next, we asked whether NPs would be effluxed by leukemic cells overtime. It is known that tumor cells high express P-glycoprotein (Pgp), a membrane transporter that is responsible for the efflux of drugs21 and nanoparticles22. Therefore, we studied by flow cytometry the effects of the Pgp antagonist verapamil22 and the endosome disruption agent chloroquine23 in the intracellular accumulation of NPs on RA-resistant Zn-induced U937-B412 cells. Our results showed that the intracellular accumulation of the NPs in U937 was similar with or without inhibition of Pgp or promoting endosomal escape by chloroquine (FIG. 2F.2). In contrast, the intracellular accumulation of control ultra small paramagnetic iron nanoparticles (USPIO) required the inhibition of Pgp (FIG. 2F.1). Overall, our results show the unique properties of our NP formulation to accumulate in leukemic cells.

To evaluate the feasibility of remotely trigger the disassembly of a specific population of NPs during their intracellular trafficking, we transfected HUVECs with Qdot525-labelled NPs (10 µg/mL) for 4 h. When a small region of the cell having NPs is excited by blue light laser (405 nm) under a confocal microscope, NP fluorescence increases as compared to a reference region not excited with UV light (FIG. 3A). This increase is due to the disassembly of the NPs and a decrease in the quenching of the quantum dots immobilized in the NPs.

The potential of the light-activatable NPs described was assessed in the control of the differentiation of leukemia cells. The differentiation of leukemia cells is a therapeutic platform very often used in the clinic to eradicate blood cancers, being the concentration of the inductive agent and the time of its application very important variables for the success of the therapy. RA was used as differentiation agent.

Figure 14:
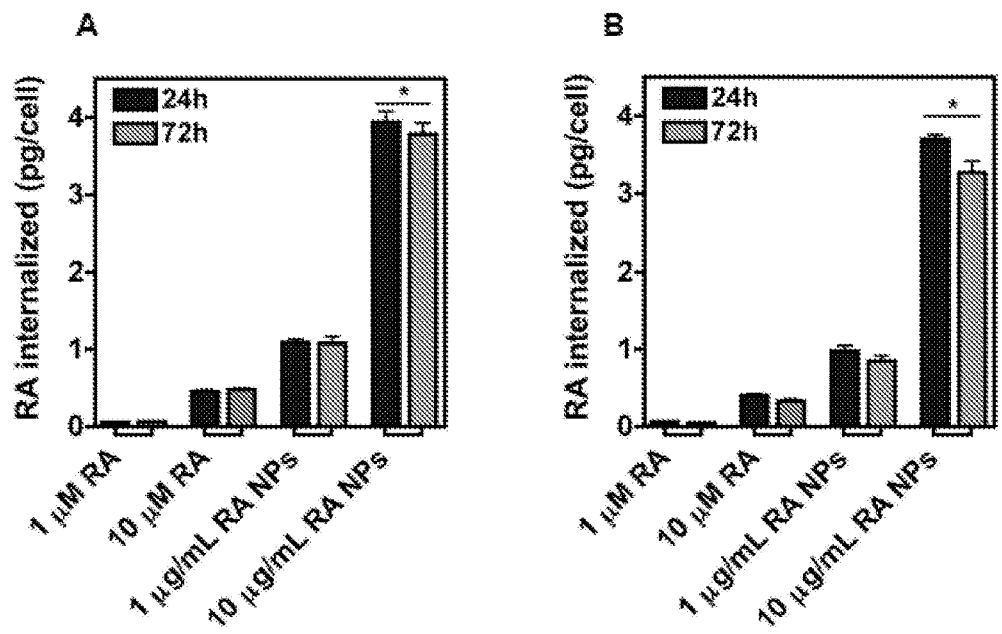
FIG. 14: Tritium-labeled retinoic acid uptake assay in K562 (A) and U937 (B) cells. K562 and U937 cells were cultured with soluble 3H-RA (1 and 10 μM) in culture medium for the entire duration of the experiment, or light-activatable 3H-RA+ NPs (1 and 10 μg/mL). NPs were added to cell culture for 4 hours. Then, the cells were washed with PBS, and fresh cell medium added and the cells remained in culture for 24/72 hours before scintillation counting.

To assess the efficiency of the RA$^+$ NPs in delivering RA inside leukemic cells and induce an RA-dependent signaling pathway a RARE reporter cell line was generated using NB4 cells. The RA-dependent induction of a RARE element driving the transcription of the firefly luciferase gene was used to evaluate the kinetics of RA-induction using RA$^+$ NPs or RA in solution. These luciferase assays showed that RA$^+$ NPs are able to induce high levels of luciferase activity shortly after light activation (FIG. 3b). RA$^+$ NPs are more efficient than RA in solution at inducing transcription from the RARE-Luciferase locus and are also quicker. In order to assess if this higher efficiency is related with a higher amount of RA being delivered inside the cells using the NPs, radioactive RA was used. Cells were incubated in the presence of [$^3$H]RA (1 uM and 10 uM) and [$^3$H]RA-NPs (1 ug/mL and 10 ug/mL) at 3° C. for 4 hours. After 24 and 72 hours, cells were washed and the amounts of [$^3$H]RA internalized were measured. Comparable results were obtained for NB4 (FIG. 3C), K562 and U937 cell lines (FIG. 14). The uptake of [$^3$H]RA was higher using the NPs when comparing with [$^3$H]RA available in solution. Considering that there was a smaller amount of RA in the NP formulation than the one available when cells were incubated with RA in solution the rational for NP utilization as a carrier for RA is well justified both from an efficiency point of view as from an uptake yield perspective (values below 2% were obtained for [$^3$H]RA in solution comparing with values above 20% obtained when nanoparticles are employed). RA uptake reached its peak at 24 h; after which there is a small decrease in the total amount of RA present in culture for longer times. Considering individual cells there is a higher decrease in the amount of RA with the time, which is probably due to proliferation of the cells along the time.

Furthermore, RA$^+$ NPs can reduce the dose of RA that very often (up to 20-30% of the patients) lead to hyperleukocytosis as well as the syndrome of respiratory distress. Complexes of RA with PEI were formed by the electrostatic interactions of the carboxyl groups of RA with the amine groups of PEI. The NP formulation contained approximately 120 µg of RA per mg of NP, had an average diameter of 160 nm and a zeta potential of 22 mV.

Figure 5:
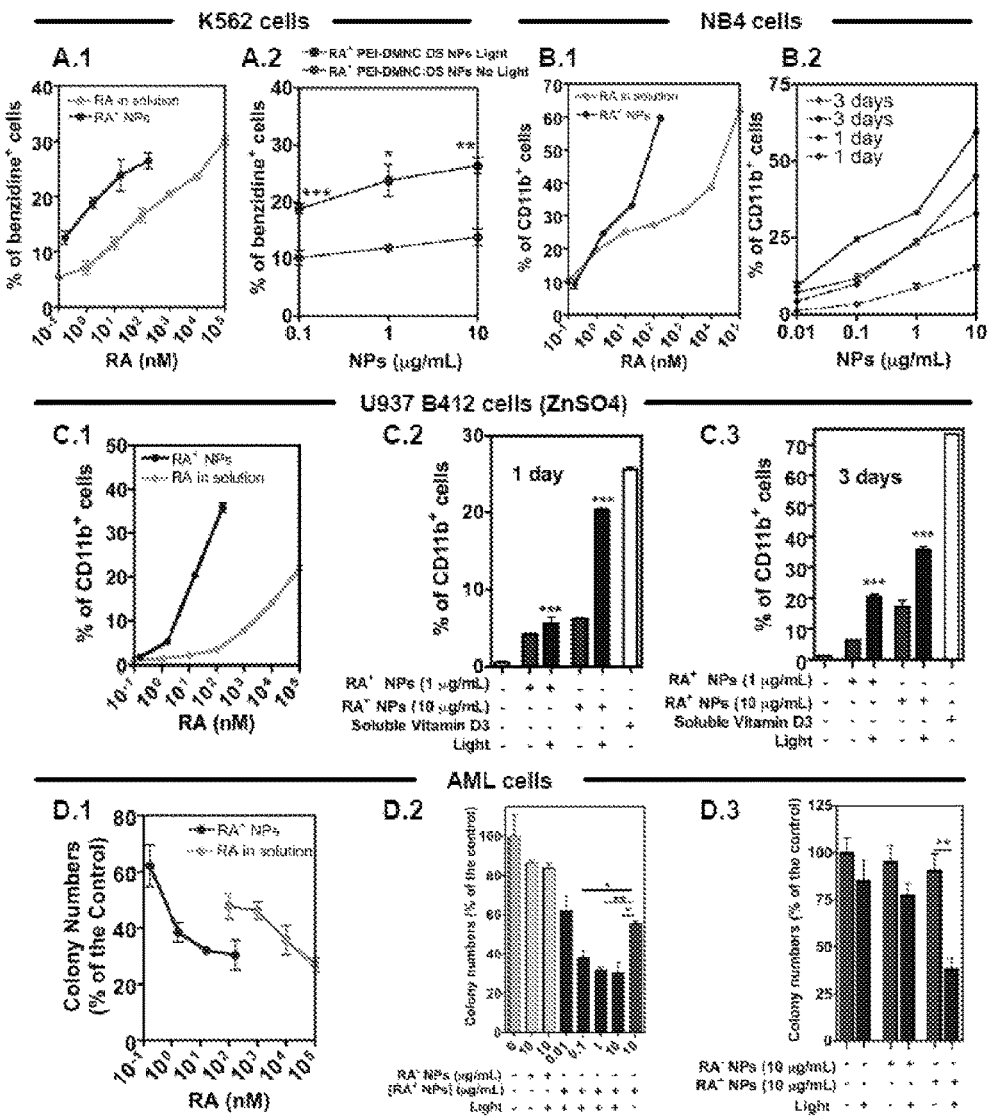
FIG. 5—In the case of cells treated with NPs, cells were treated with $RA^+$ NPs for 4 h, washed, activated or not with UV light (365 nm, 100 Watts) for 5 min, and then cultured for a certain period of time. In case of cells treated with soluble RA, cells were cultured in media containing soluble RA for the entire period of culture. (A.1) Erythroid differentiation of human leukemia K562 cells cultured with light-activated NPs or soluble RA. K562 cells were cultured for 6 days. (A.2) Percentage of benzidine$^+$ cells in K562 cells after 6 days of culture. (B.1) Myelocytic differentiation ($CD11b^+$ cells) of human leukemia NB4 cells cultured with light-activated NPs or soluble RA. NB4 cells were cultured for 3 days. (B.2) Percentage of $CD11b^+$ cells in NB4 cell cultures after 1 and 3 days of culture. (C.1) Myelocytic differentiation ($CD11b^+$ cells) of human Zn-induced U937-B412 cells cultured with light-activated NPs or soluble RA. Zn-induced U937-B412 cells were cultured for 3 days. (C.2 and C.3) Percentage of $CD11b^+$ cells in Zn-induced U937-B412 cell cultures after 1 day (C.2) or 3 days (C.3) of culture. Cells cultured with $10^{-7}$ M of vitamin D3 for 1 or 3 days were used as positive controls. (D.1 and D.2) Differentiation of AML stem cells cultured with light-activated NPs or soluble RA. Cell differentiation was evaluated by a colony forming unit assay at day 14. (D.2) AML stem cells were cultured for 14 days with RA in medium ($10^2$-$10^5$ nM) or $RA^+$ NPs (0.01-10 µg/mL) or blank NPs (10 µg/mL), exposed or not to UV light. Cell differentiation was evaluated by a colony forming unit assay at day 14. (D.3) Long-term culture-initiating cell assay results. AML stem cells were cultured on feeder layers for 5 weeks and then on methylcellulose medium for 14 days with blank NPs (10 µg/mL) or $RA^+$ NPs (10 µg/mL) exposed or not to UV light. Results are expressed as a mean percentage of control plates containing only AML cells. Results are expressed as Mean±SEM (n=3). *P<0.05, P<0.01, *P<0.001.

To further explore the therapeutic potential of light-activatable RA$^+$ NPs, human CML K562 cells were incubated for 4 h with NPs, washed, and further cultured for 1 to 3 days. K562 cells differentiate into the erythroid lineage when treated with soluble RA, although the efficiency is relatively low. The treatment of K562 with light-activated RA$^+$ NPs improved largely (from 100 up to 1000 fold) the differentiation of K562 cells, as compared to soluble RA (FIG. 5A.1). Importantly, the disassembly of RA$^+$ NPs triggered by light enhanced the differentiation process of the cells as compared to cells treated with non-activated RA$^+$ NPs (FIG. 5A.2).

Figure 1:
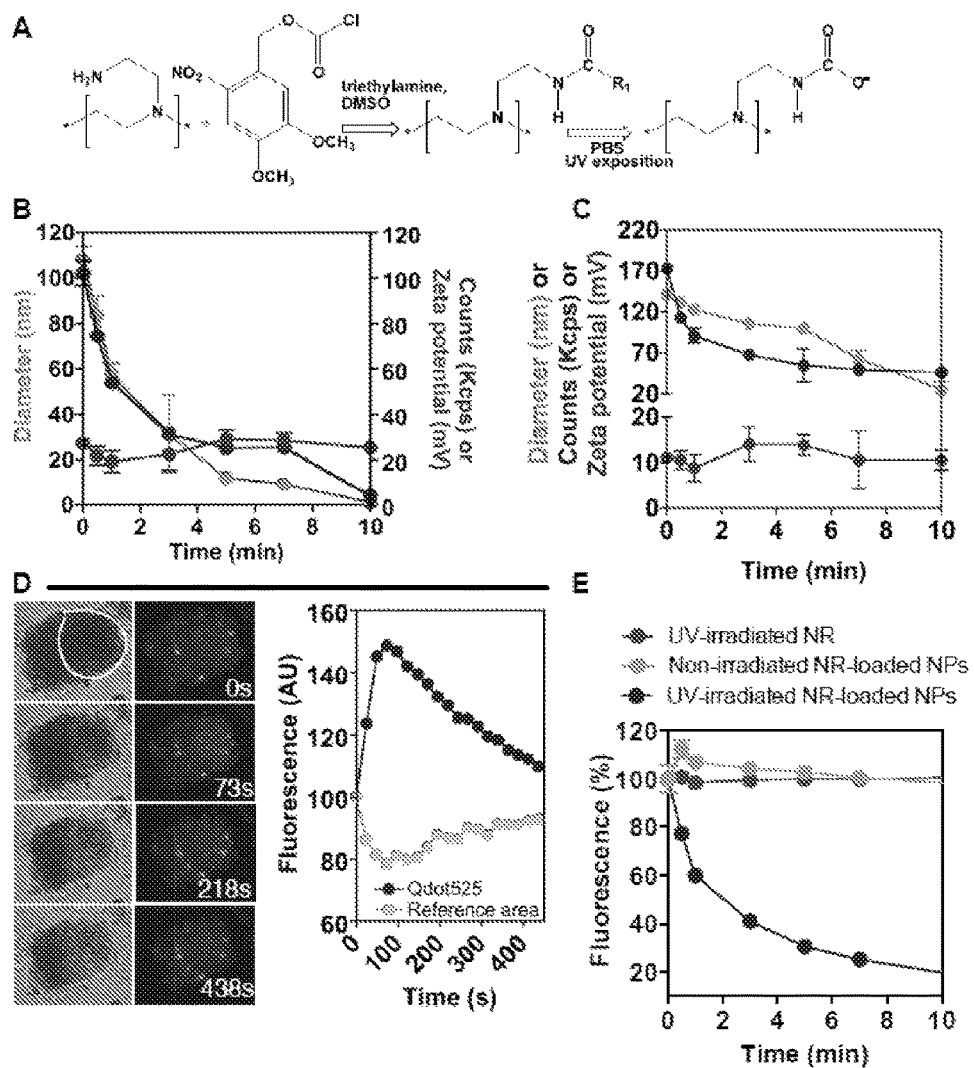
FIG. 1: Preparation of PEI derivatized with DMNC. Photo-disassembly of $PEI-DMNC_{25}$: DS NPs: (A) Schematic representation for the conjugation of PEI with DMNC and subsequent scission of the conjugate by UV light. (B) A suspension of NPs (n=3) (2 mL, 50 µg/mL in water) was exposed to UV light (365 nm, 100 Watts) for up to 10 min. At each time, the size, zeta potential and number of NPs (kcps) in the suspension was evaluated by dynamic light scattering. (C) A suspension of NPs containing NR (n=3) (2 mL, 50 µg/mL in water) was exposed to UV light (365 nm, 100 Watts) for up to 10 min. At each time, the size, zeta potential and number of NPs (kcps) in the suspension was evaluated by dynamic light scattering. (D) Confocal images showing light-disassembly of Qdot525-labeled NPs. A section of a NP aggregate (area delimited in the figure) was bleached continuously by a laser at 405 nm as confocal images were collected every 20 s. The images show the disassembly of the bleached area of the NP aggregate. Fluorescence intensity of the area bleached by the laser and reference area (i.e., not activated by the laser) overtime. (E) Normalized fluorescence vs. time for the same NR-loaded NP formulation when exposed or not to UV light (365 nm, 100 Watts), showing the increase in the release rate with UV exposure. Nile Red in aqueous solution exposed to UV light is presented to demonstrate its photostability.
Figure 2:
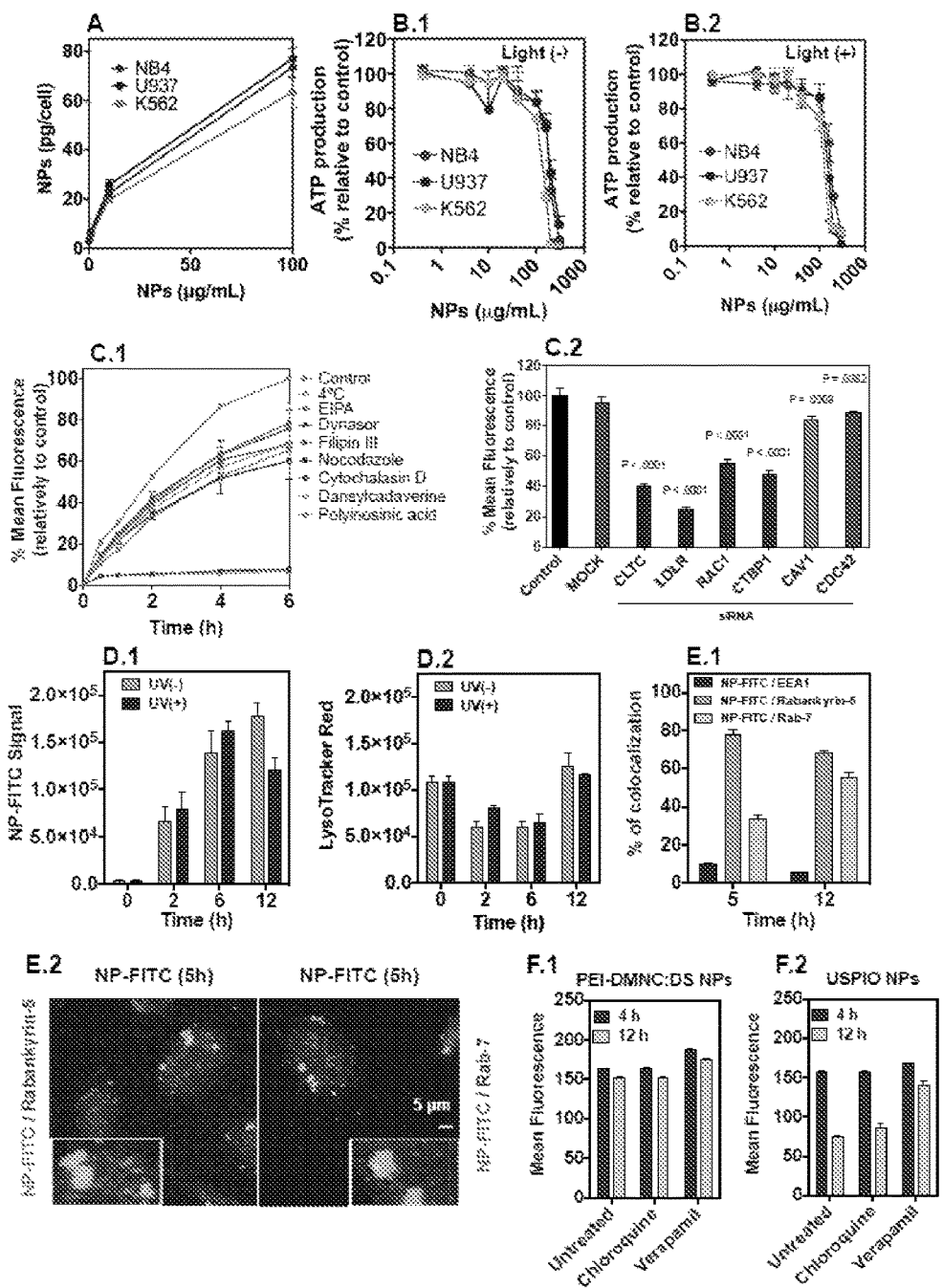
FIG. 2(A) Amount of NPs internalized by leukemia cell lines K562, NB4 and U937 as determined by ICP-MS (Zn quantification). Cells were incubated with NPs for 4 h, washed, lysed and Zn content of the NPs was quantified by ICP-MS. Results are expressed as Mean±SEM (n=3). (B) Cytotoxicity of NPs against K562, NB4 and U937 cells. Cells were cultured in medium supplemented with light-sensitive $RA^+$ NPs for 4 h, washed, exposed or not to a UV light for 10 min, and then cultured for 20 h. Cell cytotoxicity was evaluated by an ATP kit. Results are expressed as Mean±SEM (n=3). (C) Internalization mechanisms of NPs. (C.1) Uptake of TRITC-NPs by U937 cells in the presence of several endocytosis inhibitors. Results are expressed as Mean±SEM (n=3). (C.2) Uptake of TRITC-NPs in U937 cells after silencing key regulators of CME (CLTC and LDLR), caveolin-mediated endocytosis (CAV1), GEEC-CCLIC pathways (CDC42) and macropinocytosis (RAC1 and CTBP1) with siRNAs. The results are expressed as Mean±SEM (n=3). $P_{value}$ indicate significance relative to control. (D) Cellular trafficking of FITC-labeled NPs. HUVEC cells were incubated with FITC-labeled NPs (1 µg/mL) for 1 or 4 h, washed extensively, exposed or not to UV light (365 nm, 100 Watts), cultured in normal conditions for 1 or 2/8 additional hour/s, respectively, and stained with LysoTracker DND-99 before cell fixation. Results are expressed as Mean±SEM (n=3). (E) Intracellular trafficking of FITC-labelled NPs through endocytosis. Early endosome were stained with EEA1 antibody, early/late endosomes were stained with Rab-5 antibody and late endosome/lysosomes were stained with Rab7 antibody. Representative images of the intracellular distribution of FITC-labelled NPs in relation to early/late endosomes stained with Rab-5 antibodies (left image), and late endosome/lysosome stained with Rab7 antibody (right image). HUVEC cells were incubated with FITC-labelled NPs (1 µg/mL) for 4 h, washed extensively and cultured in normal conditions for 1 additional hour before cell fixation. Quantification of FITC-labelled NPs co-localized with EEA1, Rab-5 and Rab7 (right graph). HUVEC cells were incubated with 1 µg/mL for 4 hours, washed extensively and cultured in normal conditions for ⅛ additional hour's before cell fixation. Results are expressed as Mean±SEM (n=3). (F) TRITC-labelled PEI-DMNC:DS NPs (10 µg/mL) or TRITC-labelled USPIO NPs (100 µg/mL) intracellular accumulation in Zn-induced U937 cells in the presence of the Pgp antagonist verapamil and of the endosome disruption agent chloroquine. Cells were exposed to culture medium with chemical agents, FITC-labelled NPs for 4 h, cultured for additional 8 h and finally characterized by FACS. Results are expressed as Mean±SEM (n=3).
Figure 3:
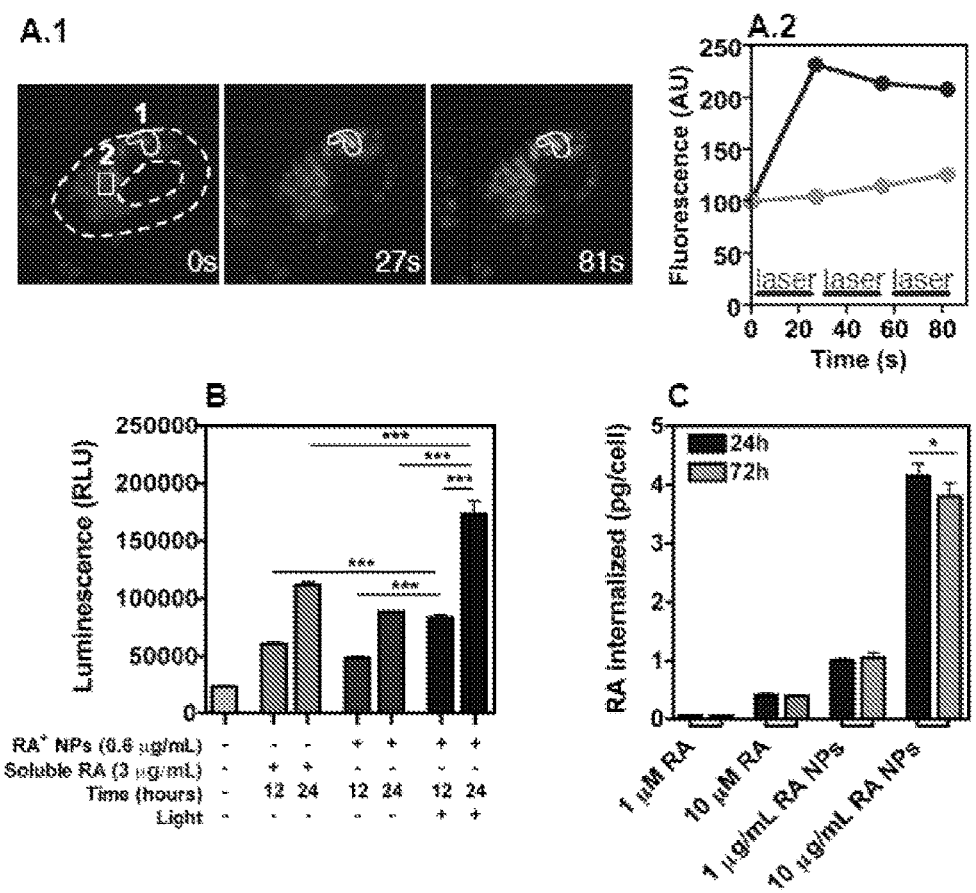
FIG. 3—(A) Confocal imaging of HUVEC cells after exposure for 4 h to QDot525-labelled NPs. A small section of the cell (region 1, created by a mask) was then exposed to blue light laser cycles (405 nm) in a Zeiss confocal microscope and the intensity of fluorescence at 525 nm monitored. In parallel, the fluorescence of another section of the cell (region 2) not excited with the laser was monitored as a control. Our results show that the fluorescence intensity in region 2 maintains overtime while in region 1 the intensity increases. Blue dots and line presents the blue light laser-exposed area of Qdot525-labelled NPs; orange dots and line presents the control unexposed area of Qdot525-labelled NPs. Dashed areas show cell membrane and nucleus. (B) Intracellular release of RA as evaluated by a RARE luciferase assay. NB4-RARE cells were cultured with soluble RA (10 µM; 3 µg of RA per mL) in culture medium for the entire duration of the experiment, or light-activatable $RA^+$ NPs (5 µg/mL; 0.6 µg of RA per mL). Cells were exposed to NPs for 1 h, washed with PBS, and resuspended in cell medium. Some samples were exposed to UV light (365 nm, 100 Watts) for 5 min. The cells were then cultured for 12/24 h before luciferase luminescence reading. Results are expressed as Mean±SEM (n=3). (C) [$^3$H]-RA uptake by NB4 cells. NB4 cells were cultured with soluble $^3$H-RA (1 and 10 µM) in culture medium for the entire duration of the experiment, or light-activatable $^3$H-$RA^+$ NPs (1 and 10 µg/mL). Cells were exposed to NPs for 4 h, cells washed with PBS and then resuspended in cell medium for additional 20/68 h before scintillation counting. Results are expressed as Mean±SEM (n=3). *P<0.05, P<0.01, *P<0.001.
Figure 4:
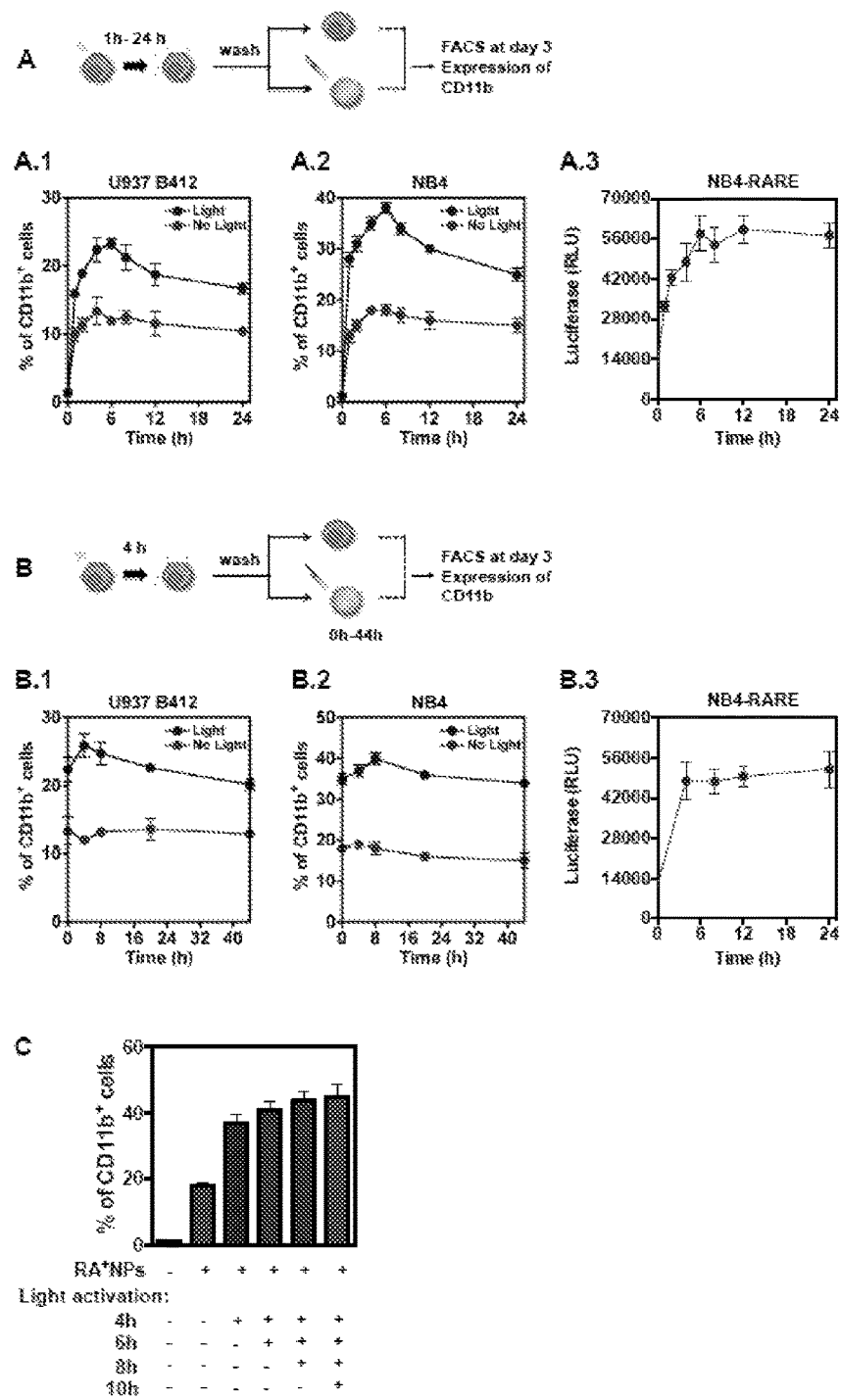
FIG. 4: Effect of time in the activation of $RA^+$ NPs within the cells. (A) Schematic representation of the methodology. Zn-induced U937-B412 (A.1), NB4 (A.2) or NB4-RARE-luciferase reporter (A.3) cells were cultured with $RA^+$ NPs (1 µg/mL) for variable period of times (1 up to 24 h), washed with PBS, resuspended in cell culture media, exposed to UV light (365 nm, 100 Watts) for 5 min, and cultured for 12 h (luciferase measurements) or 72 h (flow cytometry analyses). Results are expressed as Mean±SEM (n=3). (B) Schematic representation of the methodology. Zn-induced U937-B412 (B.1), NB4 (B.2) or NB4-RARE-luciferase reporter (B.3) cells were cultured with $RA^+$ NPs (1 µg/mL) for 4 h, washed with PBS, resuspended in cell culture media, exposed to UV light (365 nm, 100 Watts) for 5 min at variable periods of time (0 up to 44 h), and cultured for 12 h (luciferase measurements) or 72 h (flow cytometry analyses). Results are expressed as Mean±SEM (n=3). In A.3 and B.3, the activation of RA-dependent signaling pathway was measured by luminescence while cell differentiation was evaluated by the expression of CD11b. (C) Effect of multiple light activation in CD11b expression in Zn-induced U937-B412 cells. Cells were cultured with $RA^+$ NPs (10 µg/mL) for 4 h, washed with PBS, resuspended in cell culture media, exposed to multiple 5 min-cycles of UV light (365 nm, 100 Watts) during the 72 h of culture. Myelocytic differentiation ($CD11b^+$ cells) of human leukemia Zn-induced U923-B412 cells was determined by FACS. Results are expressed as Mean±SEM (n=3).
Figure 15:
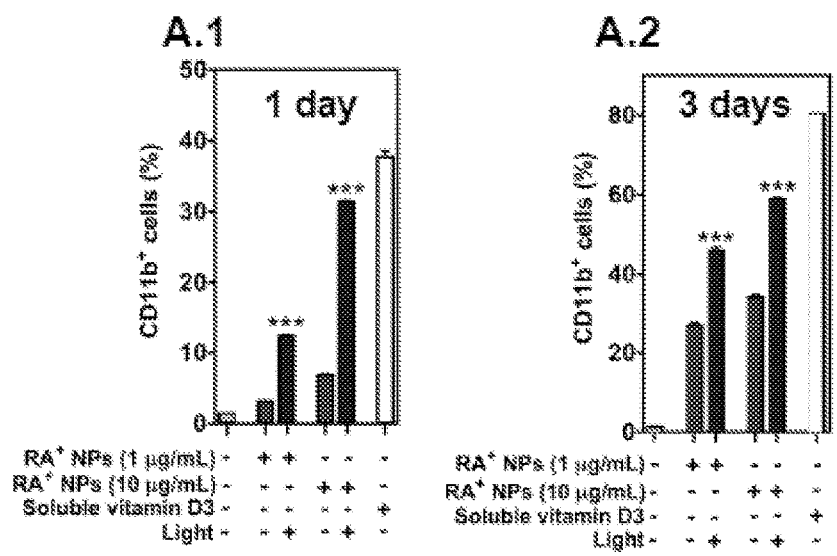
FIG. 15: Myelocytic differentiation of human leukemia U937-B412 cells without zinc-induction. (A.1) Percentage of CD11b+ cells in U937-B412 cells cultures without zinc-induction after being exposed for 1 day to various concentrations of light sensitive RA+ NPs, exposed or not to UV light (365 nm, 100 Watts, 5 min) after a 4 h-period of internalization and 1300 rpm centrifugation washing step, or cultured with 10-7 M of vitamin D3 (Sigma) in culture medium during 1 day. (A.2) Percentage of CD11b+ cells in U937-B412 cells cultures without zinc-induction after being exposed for 3 day to various concentrations of light sensitive RA+ NPs, exposed or not to UV light (365 nm, 100 Watts, 10 min) after a 4 h-period of internalization and 1300 rpm centrifugation washing step, or cultured with 10-7 M of vitamin D3 (Sigma) in culture medium during 3 day.

Next, the therapeutic effect of the light-activatable RA$^+$ NPs was evaluated in human acute promyelocytic leukemia (APL) cells. APL is a subtype of myeloid leukemia that comprises 10 to 15% of patients with acute myeloid leukemia (AML) and it is characterized by a unique translocation between chromosomes 15 and 17. The translocation causes the fusion of 2 genes, PML and RARα, leading to the aberrant fusion protein PML-RARα which disrupts the function of both normal PML and RARα. It has been shown that RA can induce the degradation of the PML-RARα and induce cell differentiation. The effect of soluble RA and light-sensitive RA$^+$ NPs was examined in the induction of APL-derived NB4 cells differentiation by assessing CD11b expression, a marker of myeloid differentiation. RA$^+$ NPs were much more effective (from 100 up to 1000 fold) in the differentiation of leukemia cells than soluble RA (FIG. 5B1). Furthermore, cells treated with RA$^+$ NPs activated by light showed higher (from 1.5 to 2 fold) differentiation into the myeloid lineage than cells treated with non-activated RA$^+$ NPs (FIG. 5B2). Importantly, the differentiation effect exerted by the NPs is mediated by the intracellular delivery of RA since the supernatant of NPs suspended in media for 6 days at 37° C. had no significant effect in the differentiation of NB4 cells. The differentiation capacity of light-activatable RA$^+$ NPs was evaluated in APL cells having chimeric PLZF/RARα fusion protein resulting from a translocation between chromosomes 11 and 17. APL caused by PLZF/RARα is morphologically indistinguishable from APL caused by PML/RARα and exhibits impaired sensitivity to RA. The differentiation of a U937 promonocytic leukemia clone transduced with a zinc-inducible U937 cell system expressing the PLZF/RARA fusion protein (U937-B412) was analyzed. The results show that the induction of PLZF/RARα expression by zinc in U937-B412 cells decreases their ability to differentiate into myeloid cells (CD11b$^+$ cells) as compared to cells without PLZF/RARα expression (FIG. 5C and FIG. 15). However, U937-B412 cells treated with RA$^+$ NPs were more prone to differentiate into myeloid cells (approximately 1000 fold) than cells treated soluble RA (FIG. 5C1). Moreover, cells treated with light-activated RA$^+$ NPs show higher (from 2 to 4 fold depending in the differentiation time and NP concentration)

capacity for myelocytic differentiation than cells treated with non-activated RA⁺ NPs (FIGS. 5C2 and 5C3). The results seem to indicate that the intracellular concentration of released RA saturates the RAR and RXR available on the cell overcoming the transcription repression induced by PLZF/RARα protein.

To further validate the potential of the opto-nanomedicine approach bone marrow aspirates from human patients with AML were treated and their clonogenic potential was evaluated by the colony-forming cell (CFC) and long-term culture-initiating cell (LTC-IC) assays. AML encompasses functionally diverse cells originating from a leukemic stem cell (LSC). LSCs initiate and sustain the AML clonal hierarchy and possess biological properties rendering them resistant to conventional chemotherapy. Initially, CD34⁺ cells were isolated from bone marrow by FACS and sorted cells treated with RA⁺ NPs or soluble RA. Our results indicate that light-activatable RA⁺ NPs were higher effective than soluble RA in decreasing the number of CFCs (from 100 to 1000 fold) (FIG. 5D1). Cell treatment with blank nanoparticles (RA⁻ NPs) activated or not with light had no significant effect in the CFC number relatively to control (FIG. 5D2). Results further indicate that RA⁺ NPs activated by light are more effective in decreasing the number of CFCs as well as LTC-ICs (FIG. 5D3) as non-activated RA⁺ NPs.

Figure 6:
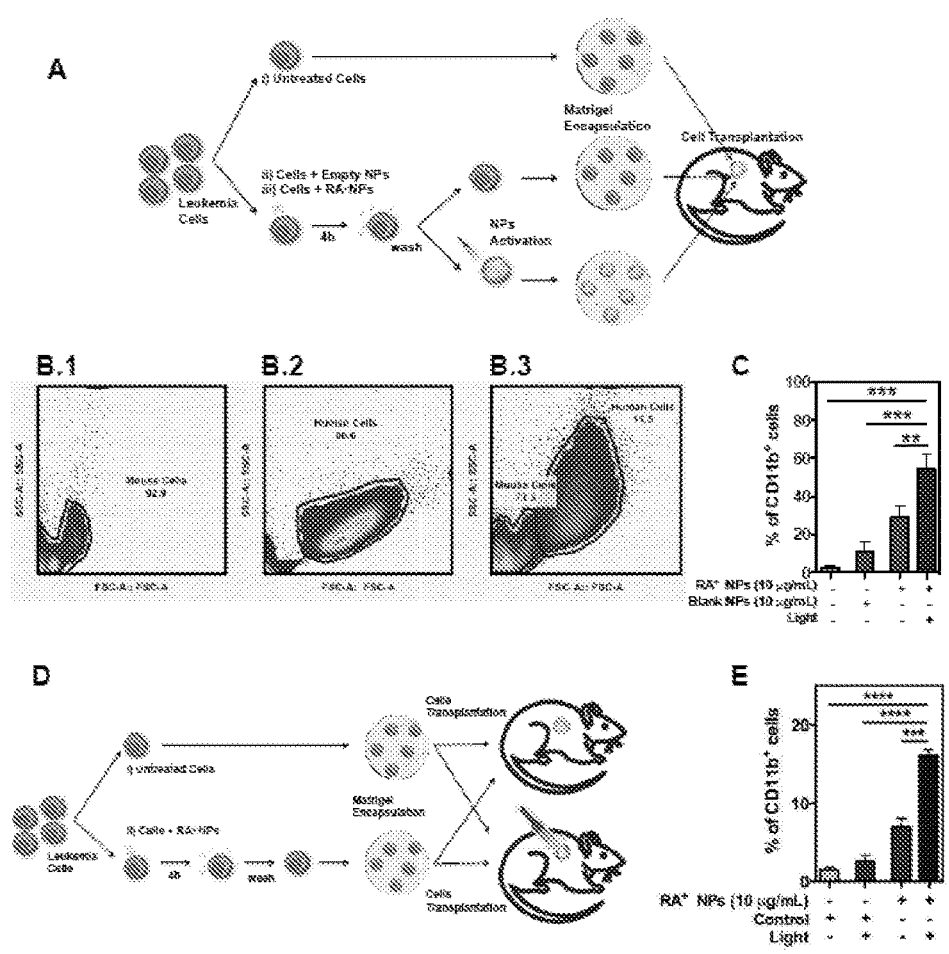
FIG. 6—In vivo differentiation of NB4 cells exposed to light-activatable RA+ NPs. (A) Schematic representation of the in vivo experimental set up. Cells were treated with blank or RA+ NPs (10 μg/mL) for 4 h, washed, and then activated or not with a blue optical fiber (405 nm, 80 mW) for 5 min. Cells were then resuspended in a 1:1 (v/v) Matrigel solution and subcutaneously injected in a PDMS cylinder construct implanted in the dorsal region of mice. After 5 days, cells were removed from the construct and characterized by FACS, for CD11b expression. (B) Representative flow cytometry plots. Representative flow cytometry plots showing mice recipient cells (B.1), human leukemia NB4 cells (B.2) and a mixture of mice recipient cells with human leukemia NB4 cells (B.3). (C) Percentage of CD11b+ cells in human leukemia NB4 cells collected 5 days after subcutaneously injection. Results are expressed as Mean±SEM (n=4). *P<0.05, P<0.01, *P<0.001. (D) Schematic representation of the in vivo set up. Cells were treated with RA+ NPs (10 μg/mL) for 4 h, washed and then encapsulated in a 1:1 (v/v) Matrigel solution and subcutaneously injected in a PDMS cylinder construct implanted in the dorsal region of mice. After 24 h, some experimental groups were activated in vivo with a blue optical fiber for 5 min. (E) Percentage of CD11b+ cells in human leukemia NB4 cells collected 3 days after the in vivo activation. Results are expressed as Mean±SEM (n=3). *P<0.001, **P<0.0001.

Next, we evaluated if RA⁺ NPs can function in vivo. NB4 cells were cultured with RA⁺ NPs for 4 h, washed and activated ex-vivo by exposure to a 405 nm blue laser (80 mW) for 5 min, embedded in Matrigel and then injected into a cylindrical poly(dimethylsiloxane) (PDMS) construct that has been previously implanted subcutaneously in NOD/SCID recipients (FIG. 6A). The PDMS cylinder was used to restrict cell position inside the animal. After 5 days, human cells were isolated from the implants and CD11b expression measured by flow cytometry (FIGS. 6B.1-6B.3). Consistent with the in vitro data, CD11b expression was statistical higher in NB4 cells treated with ex vivo light-activated RA⁺ NPs than in cells treated with RA⁺ NPs without light activation (FIG. 6C). The experiment was then repeated but this time with in vivo activation. One day after implantation the recipients were exposed to a 405 nm blue optical fibre for 5 min at the sites of the implants that contained the cells (FIG. 6D). After 3 days the recipients were sacrificed, human cells isolated and CD11b expression was assessed. CD11b expression was higher in NB4 cells from mice that had been exposed to the blue laser demonstrating that internalised RA⁺ NPs can be activated to release RA in vivo in a highly controlled manner (FIG. 6E).

METHODS

Preparation and Characterization of Poly(Ethyleneimine) (PEI) Conjugated with 4,5-dimethoxy-2-nitrobenzyl chloroformate (DMNC)

DMNC (DS100: 194.1 mg; DS25: 48.5 mg, Sigma) was slowly added to a solution of PEI in DMSO (2 mL containing 50 mg/mL PEI, Sigma) containing triethylamine (DS100: 98.2 µL; D25: 24.5 µL, Sigma), and the reaction flask cooled to 0° C. by immersion on ice. Then, the reaction was allowed to proceed for 24 h at 25° C. with stirring. At the end, the PEI-DMNC conjugate was purified by dialysis (Spectra/Por® 1 Regenerated Cellulose dialysis membrane, MWCO 6000-8000 Da, Spectrum) against DMSO overnight at room temperature. Reaction yields above 54% were obtained using a dialysis purification methodology. For NMR characterization, PEI-DMNC (in DMSO) was precipitated in water, washed, freeze-dried, and then dissolved (10 mg/mL) in DMSO-d6 and ¹H NMR spectra were acquired using a Bruker Avance III 400 MHz spectrometer.

Preparation of NPs

Non-activatable NPs were prepared by the electrostatic interaction of PEI (polycation) with dextran sulfate (DS, polyanion) in water, at room temperature, as previously described by us (Maia, J. et al. Controlling the neuronal differentiation of stem cells by the intracellular delivery of retinoic acid-loaded nanoparticles. ACS Nano 5, 97-106 (2011)). Briefly, an aqueous DS solution (1 mL, 10 mg/mL) was added drop-by-drop to an aqueous solution of PEI (5 mL, 10 mg/mL) and stirred for 5 min. Then, an aqueous solution of $ZnSO_4$ (0.6 mL; 1 M) was added and stirred for 30 min. The NP suspension was then dialyzed (Spectra/Por® 1 regenerated cellulose dialysis membrane, MWCO 6000-8000 Da, Spectrum) for 24 h, in the dark, against an aqueous solution of mannitol (5%, w/v), lyophilized for 1 day and stored at 4° C. before use.

Light-activatable NPs were prepared by adding a PEI-DMNC solution (66.7 µL, 150 mg/mL, in DMSO) to an aqueous solution of DS (5 mL, 0.4 mg/mL) and stirred for 5 min. Then, an aqueous solution of $ZnSO_4$ (120 µL, 1 M) was added and stirred for 30 min. The NP suspension was then dialyzed (Spectra/Por® 1 Regenerated Cellulose dialysis membrane, MWCO 6000-8000 Da, Spectrum) for 24 h, in the dark, against an aqueous solution of mannitol (5%, w/v), lyophilized for 1 day and stored at 4° C. before use. In some cases, PEI-DMNC was labeled with Qdot525. For that purpose, an aqueous solution of 1-ethyl-3-(3-dimethylaminopropyl)carbodiimide hydrochloride (EDC; 500 µL of EDC (10 mg/mL, aqueous solution at pH 6.0)) was added to a suspension of Qdots525 (0.16 mmoles, in 310 µL of PBS). After 5 min, PEI-DMNC solution (200 µL, 25 mg/mL in DMSO) was added to the previous solution and allowed to react for 1 h, in the absence of light, at room temperature.

For the preparation of NR-containing NPs, initially a NR solution (60 µL, 2% w/v, in DMSO) was added to a solution of PEI-DMNC (66.7 µL, 150 mg/mL in DMSO) and maintained at room temperature for 30 min, under stirring. The solution was then carefully added to an aqueous solution of DS (5 mL, 0.4 mg/mL) and stirred for 5 min. The NPs in suspension were treated with an aqueous solution of $ZnSO_4$ (120 µL; 1 M) for 30 min. NR that was not encapsulated in the NPs was removed by centrifugation (2,000 g for 3 min). The NP suspension was then dialyzed (Spectra/Por® 1 Regenerated Cellulose dialysis membrane, MWCO 6000-8000 Da, Spectrum) for 24 h, in the dark, against an aqueous solution of mannitol (5%, w/v), lyophilized for 1 day and stored at 4° C. before use. For the preparation of RA-containing NPs, a RA solution (24 µL, 50 mg/mL, in DMSO) was added to a solution of PEI-DMNC (66.7 µL, 150 mg/mL in DMSO). The subsequent steps were similar to the ones described above for NR-containing NPs.

For the preparation of fluorescently labelled NPs, NPs (2 mg) were resuspended in 0.1 M carbonate/bicarbonate buffer (1 mL, pH 8.3) followed by the addition of FITC or TRITC (5 µL in DMSO, 3-fold molar excess). The NP suspension was stirred for 1 h in the absence of light and then dialyzed (Spectra/Por® 1 regenerated cellulose dialysis membrane, MWCO 6000-8000 Da, Spectrum) for 24 h against an aqueous solution of mannitol (5%, w/v), lyophilized, and stored at 4° C. before use.

Characterization of the NPs

In an endodiment, the diameter of the NPs was measured by photon correlation spectroscopy (PCS) using quasi-elastic light scattering equipment (Zeta-Pals™ Zeta Potential Analyzer, Brookhaven Instruments Corp., Holtsville, N.Y.) and ZetaPlus™ Particle Sizing Software (version 4.03). To measure NP diameter, the NP suspension (2 mL, 50 μg/mL in water for molecular biology) was added to a cuvette and allowed to stabilize for 10 min. The sample was then vortexed for 5 s and subjected to NP size analysis in the ZetaPlus™ for 3 min (3 times; all data were recorded at 90°). After each reading the cuvette was again vortexed for 5 s and exposed to UV light (365 nm) or blue light (405 nm) for a certain period of time (see above). The values of NP diameter and NP counts were recorded. The average diameters described in this work are number-weighted average diameters. The zeta potential of NPs was determined in a 1 mM KCl pH 6 solution, at 25° C. (2 mL, 50 μg/mL). All data were recorded with at least 5 runs (in triplicate) with a relative residual value (measure of data fit quality) of 0.03 mm.

In an embodiment, the diameter of NPs was also confirmed by ultra-high-resolution analytical FE-SEM SU-70 with a dedicated detector of STEM. Diluted NP suspensions (in $H_2O$) were placed on a 400-mesh 3 mm copper grid coated with a carbon support film (Taab Labs Ltd.) and dried overnight.

Cell Culture

Human umbilical vascular endothelial cells (HUVECs) were obtained from Lonza and cultured in EGM-2 medium (Lonza) in a $CO_2$ incubator at 3° C., 5% $CO_2$ in a humidified atmosphere, with media changes performed every other day. Cells were passaged every 2-5 days and used for experiments between passage 4 and 6. Human chronic myelogenous leukemia K562 cells, kindly provided by Dr. Veronica Buckle (Weatherall Institute of Molecular Medicine) were cultured in RPMI-1640 (Gibco) in a $CO_2$ incubator at 3° C., 5% $CO_2$ in a humidified atmosphere, supplemented with 10% fetal bovine serum (Gibco) and 100 U/mL PenStrep (Lonza). Human bone marrow acute promyelocytic leukemia NB4 cells, kindly provided by Dr. Arthur Zelent (Institute of Cancer Research, Royal Cancer Hospital) were cultured in RPMI-1640 (Gibco) in a $CO_2$ incubator at 3° C., 5% $CO_2$ in a humidified atmosphere, supplemented with 10% fetal bovine serum (Gibco) and 100 U/mL PenStrep (Lonza). Human myelomonoblastic cell lines U937-MT and U937-B412 (Ruthardt, M., et al. Opposite effects of the acute promyelocytic leukemia PML-retinoic acid recpetor alpha (RAR alpha) and PLZF-RAR alpha fusion proteins on retinoic acid signalling. Mol Cell Biol 17 (8), 4859-4869 (1997)), kindly provided by Dr. Estelle Duprez (Centre de Recherche en Cancérologie de Marseille, France), were maintained at exponential growth in RPMI-1640 medium supplemented with 10% fetal bovine serum and 100 U/mL of PenStrep. U937-MT is the empty vector control and U937-B412 contains PLZF/RARA cDNA under the control of the zinc inducible human-metallothionein promoter (Ruthardt, M., et al. Opposite effects of the acute promyelocytic leukemia PML-retinoic acid recpetor alpha (RAR alpha) and PLZF-RAR alpha fusion proteins on retinoic acid signalling. Mol Cell Biol 17 (8), 4859-4869 (1997)). For PLZF/RARA induction cells were stimulated with 0.1 mM $ZnSO_4$ for at least 24 h.

DNA Damage Induced by Light. NPs Cytotoxicity, Internalization, Uptake, Intracellular Trafficking and Accumulation Studies Assessment of histone γH2AX phosporylation (DNA damage) induced by UV light or blue light irradiation. To assess histone γH2AX phosporylation (DNA damage) induced by UV light or blue light irradiation, HUVEC cells (passage 4) were cultured on 1% gelatin-coated slides until subconfluency in EGM-2, followed by exposure to UV light (365 nm, 100 Watts) or blue light (405 nm, 80 mW) for 1, 3, 5, 10, 15, 30 or 60 min, in triplicates. Control conditions did not receive any light radiation. Following treatment, the medium was replaced by fresh medium and the cells were incubated for additional 6 h on normal culture conditions. The cells were then fixed with 4% paraformaldehyde (Electron Microscopy Sciences) for 10 min at room temperature and then washed with PBS. The cells were then permeabilized with 1% (v/v) Triton-X, blocked with PBS+2% BSA and stained for 1 h with anti-human primary γH2AX antibody (clone: N1-431, BD Biosciences). Detection was done with secondary antibody anti-mouse Cy3 conjugate (Jackson ImmunoResearch). Cell nuclei were stained with 4',6-diamidino-2-phenylindole (DAPI) (Sigma), and the slides were mounted with mounting medium (Dako) and examined with a Zeiss inverted fluorescence microscope.

NP cytotoxicity analysis. To evaluate NP cytotoxicity, NPs were suspended in a solution of milli-Q water with PenStrep (5 μL/mL of 10000 U/mL stock solution, Lonza) and Fungizone (2.5 μg/mL, Sigma-Aldrich) for 30 min, centrifuged (14,000 g for 10 min), and finally resuspended in serum free cell culture medium. K562, NB4 and U937 cells ($0.1 \times 10^6$ cells/condition) were incubated in serum free RPMI-1640 for 4 h in a 96-well plate containing variable amounts of PEI-DMNC:DS NPs. Once the incubations were terminated the cells were washed gently with medium to remove NP excess, and half of the samples were exposed to UV light (365 nm, 100 Watts) for 10 min. The cells were then cultured for 20 h in 100 μL of complete medium (RPMI-1640 medium supplemented with 10% fetal bovine serum and 100 U/mL PenStrep). A CellTiter-Glo® luminescent cell viability assay (ATP, Promega, Wis., USA) was performed according to the recommendations of the vendor.

NP internalization analysis. NP internalization studies were performed in K562 and AML cells derived from bone marrow aspirates. K562 or AML cells ($0.1 \times 10^6$ cells/condition) were incubated for 4 h in serum free RPMI-1640 or serum free Ex-Vivo medium (Lonza) containing NPs (10 μg/mL), respectively, in a 6 well plate. Once the incubations were terminated, the cells were centrifuged at 1300 rpm, 2° C. for 5 min, washed one time with cold trypan blue solution (200 μL; 600 μg/mL), re-washed 3 times with cold PBS and then resuspended in PBS containing 2.5% FBS (500 μL), ready for FACS analysis. A total of 10,000 events were recorded per measurement. In some conditions, AML cells were cultured in StemSpan SFEM (Stemcell Technologies) supplemented with a human cytokine cocktail containing SCF (50 ng/mL, Stemcell Technologies), TPO (15 ng/mL) and Flt-3L (50 ng/mL, PeproTech) plus PenStrep (10,000 U/mL, Lonza) and Fungizone (25 μg/mL, Sigma) for 5 days after NPs internalization for 4 h.

NP internalization was also monitored by inductive coupled plasma mass spectrometry (ICP-MS). In this case, the intracellular levels of Zn were measured before and after cell exposure to NPs. K562, NB4 and U937 cells ($0.1 \times 10^6$ cells/well) were plated in 24 well plates and incubated in serum free RPMI-1640 from 1 to 24 h with variable amounts of PEI-DMNC:DS NPs. After incubations, NPs that have were not internalized by the cells were washed three times with PBS an the cells centrifuged followed by the addition of an aqueous solution of nitric acid (1 mL, 69% (v/v)). The samples (n=3) were analyzed by ICP-MS for the concentration of intracellular levels of Zn. The concentration of Zn was normalized per cell. The estimation of NPs was done based on controlled standard solutions.

Uptake mechanisms analysis. For determining the uptake mechanism(s), we first perform NP uptake assays in the presence of endocytosis inhibitors. U937 cells were cultured on 24 well plates ($1\times10^5$ cells/well) and inhibited by one of the following chemicals during 30 min before adding a suspension of TRITC-labelled NPs (5 µg/mL): dynasor (80 µM), cytochalasin D (10 µM), nocodazole (50 uM), filipin III (100 µM) and polyinosinic acid (100 µg/mL). The inhibitor concentrations were based in values reported in literature and further validated by us to have no cytotoxic effect over the period of the assay (6 h), as confirmed by ATP assay. The incubation of the cells with NPs for different times was performed in the presence of the inhibitor. As controls, we used cells without NPs and cells incubated with NPs without inhibitor. At the end of each time point, cells were centrifuged at 1300 rpm, 2° C. for 5 min with PBS, washed one time with cold trypan blue solution (200 µL; 600 µg/mL), re-washed 3 times with cold PBS and then resuspended in PBS containing 2.5% FBS (500 µL) for FACS analysis. A total of 10,000 events were obtained per measurement. To validate the inhibitory activity of dynasor we performed uptake studies of FITC-labeled transferrin, known to selectively enter cells via clatherin-mediated endocytosis. Briefly, U937 cells were cultured on 24 well plates ($1\times10^5$ cells/well) and treated or not with dynasor (80 µM, 30 min pre-incubation), followed by addition of 1 µg/mL FITC-labeled transferrin (Life Technologies). The transferrin was allowed to bind for 3 min at 4° C. Cells were then evaluated as before.

The NP uptake mechanism was also studied on U937 cells by silencing specific proteins of clathrin-mediated endocytosis (CLTC and LDLR), caveolin-mediated endocytosis (CAV1), GEEC-CCLIC pathways (CDC42) and macropinocytosis (RAC1 and CTBP1) by siRNA (Thermo Fisher). Transfection was performed in a 24 well plate with $0.5\times10^5$ cells in antibiotic-free complete medium with 100 nM siRNA and 1.5 µL of Lipofectamine RNAiMAX (Life Technologies) transfection reagent for 24 h. After this initial period, the transfection medium was replaced by complete medium and the cells incubated for another 48 h. Then, cells were cultured with TRITC-labelled NPs (5 µg/mL) for 6 h. Once the incubations were terminated, the cells were centrifuged at 1300 rpm, 20° C. for 5 min, with PBS, washed one time with cold trypan blue solution (200 µL; 600 µg/mL), re-washed 3 times with cold PBS and then resuspended in PBS containing 2.5% FBS (500 µL) for FACS analysis. Non-transfected cells or cells transfected with lipofectamine but without siRNAs (MOCK) were used as controls. In all FACS analysis, a total of 10,000 events were recorded per run. All conditions were performed in triplicate.

Intracellular trafficking analysis. HUVEC cells (passage 4) were cultured on 1% gelatin-coated slides until subconfluency in EGM-2. The cells were then incubated with 1 µg/mL FITC-labeled NPs for 1 or 4 hours, washed extensively, exposed or not to UV light (365 nm, 100 Watts), cultured in normal conditions for 1 or 2/8 additional hour/s, respectively. For LysoTracker staining, at time points 2, 6 and 12 hours, the cells were incubated with 50 nM LysoTracker Red DND-99 (Invitrogen). After 30 min of incubation, the coverslips were washed extensively with PBS, followed by cell fixation with 4% paraformaldehyde (Electron Microscopy Sciences) for 10 min at room temperature and then washed with PBS. Cell nuclei were stained with 4',6-diamidino-2-phenylindole (DAPI) (Sigma), and the slides were mounted with mounting medium (Dako) and examined with a Zeiss LSM 50 confocal microscope.

Co-localization analysis was performed by culturing HUVEC cells (passage 4) on 1% gelatin-coated slides until subconfluency in EGM-2. Cells were treated with 1 µg/mL FITC-labeled NPs for 1 or 4 hours, washed extensively and cultured in normal conditions for 1 or 1/8 additional hour/s, respectively. Then the cells were fixed with 4% paraformaldehyde (Electron Microscopy Sciences) for 10 min at room temperature, blocked with 2% (w/v) BSA, and when necessary, permeabilized with 0.5% (v/v) Triton-X. Cells were then stained for 1 h with anti-human primary antibodies (EEA1, clone: C45B10, Cell Signaling), Rabankyrin-5 (ANKFY1 (D-15), Santa Cruz Biotechnology), or Rab 7 (clone: D95F2, Cell Signaling). In each immunofluorescence experiment, an isotype-matched IgG control was used. Binding of primary antibodies to specific cells was detected with anti-rabbit or anti-goat IgG Cy3 conjugate (Jackson ImmunoResearch). Cell nuclei were stained with 4',6-diamidino-2-phenylindole (DAPI) (Sigma), and the slides were mounted with mounting medium (Dako) and examined with a Zeiss LSM 50 confocal microscope. Co-localization analysis was done in ImageJ through assessment of the percentage of overlapping objects. Two objects are considered to be co-localizing when their intensity profile is overlapping more than 40%. For this analysis the number (percentage of FITC-labeled NPs foci that are positive for EEA-1/Rab-5/Rab-7) and the intensity volume (percentage of FITC-labeled NPs in the EEA-1/Rab-5/Rab-7-positive compartments) were used. This approach was found to be more adequate than classical co-localization tools in ImajeJ or other softwares that measure pixel co-occurrence and correlation analyses, because it allowed us to (i) discriminate between background and vesicle/NP-foci fluorescence and (ii) interpret the results in terms of percentage of NP-foci that are localized to vesicles in another channel of interest.

Intracellular NPs accumulation analysis. To determine exocytose of NPs, NP uptake assays were performed in the presence of Pgp antagonist verapamil or the endosome disruption agent chloroquine. U937 cells were cultured on 24 well plates ($1\times10^5$ cells/well) and chloroquine (100 µM, no pre-incubation) and verapamil (100 µM, 60 min pre-incubation) conditions were tested. The chemical agents concentrations were based on values reported in the literature and further validated by us to have no cytotoxic effect over the period of the assay (12 h). After the pre-incubation with the chemical agents, TRITC-labelled PEI-DMNC:DS NPs (10 µg/mL) or TRITC-labelled poly-L-lysine USPIO NPs (100 µg/mL) were added to the cells, maintaining the chemical agents concentration. As controls we used cells incubated without NPs and cells incubated with NPs without chemical agents. At the end of each experiment, the cells were centrifuged at 1300 rpm, 2° C. for 5 min with PBS, washed one time with cold trypan blue solution (200 µL; 600 µg/mL), re-washed 3 times with cold PBS and then resuspended in PBS containing 2.5% FBS (500 µL) for FACS analysis. A total of 10,000 events were recorded per measurement, and all conditions were performed in triplicate.

RARE Cell Line Generation

The cignal lenti RARE reporter kit (CLS-016L SABiosciences) was used for the establishment of a RA reporter NB4 cell line. For that purpose, rectronectin solution (15 µg/cm², 30 µg, 500 µL on PBS, Takara) was plated in a 24-well plate 2 hours prior to cell seeding. The plate was kept at room temperature and was washed one time, immediately before seeding, with PBS. NB4 cells ($1\times10^5$) were plated in 175 µL of RPMI-1640 medium (Gibco) supplemented with 0.5% FBS and 100 U/mL PenStrep and to this condition 125 µL of cignal lentiviral particles were added to a total experimental volume of 300 µL. After a gentle swirl of the plate the cells were incubated 20 hours at 3° C. in a humidified incubator with 5% $CO_2$ atmosphere. In the following day, cells were washed and allowed to recover in the incubator for 24 hours cultured in 500 µL of fresh RPMI-1640 medium supplemented with 10% FBS and 100 U/mL PenStrep. After that, 2 µg/mL of puromycin (Invitrogen) was added to the culture medium for selection of transduced cells. Evaluation of selection efficiency in puromycin-containing medium was performed every 3 days for a period of 5 weeks.

Luciferase Assay

To assess the biological effect of RA in RAR-regulated signalling pathway activity, luciferase reporter assay was performed. NB4-RARE cells ($2.5 \times 10^4$ cells/condition) were plated in v-shaped 96-well plates and cultured with soluble RA (10 µM) or light-activatable $RA^+$ NPs (5 µg/mL). The NPs were suspended in serum free medium and added to cells for 1 h. The cells were then washed by centrifugation (1300 rpm, 5 min) to remove non-internalized NPs, and half of the samples were exposed to blue light (405 nm, 80 mW, 5 min). The cells were then cultured for 12/24 hours in RPMI-1640 medium supplemented with 10% fetal bovine serum and 100 U/mL PenStrep. After these incubation times, the conditions were centrifuged (1500 rpm, 3 min), excess medium carefully aspirated and the cells washed with 100 uL of PBS. After a new centrifugation and removal of PBS, 60 uL of cell lysis buffer (8 mM of magnesium chloride; 1 mM DL-Dithiothreitol; 1 mM Ethylenediaminetetraacetic acid; 25 mM of 1 M Trizma Base with 1 M Sodium phosphate monobasic; 15% Glycerol; and 1% Triton X-100), was added to each condition. The plate was kept on ice, under agitation for 15 min to allow complete lysis and then the plate was placed on −8° C. for the amount of time necessary for the samples to freeze. After these steps, the plate was removed from the −8° C., put on ice and allowed to defrost at slow rate.

For the preparation of the luminescence reading, 40 µL of ATP (100 µM, Sigma) was added to 1960 µL of reading buffer solution (8 mM of magnesium chloride; 1 mM DL-Dithiothreitol; 1 mM Ethylenediaminetetraacetic acid; 25 mM of 1 M Trizma Base with 1 M Sodium phosphate monobasic; and 15% Glycerol) to a final concentration of 2 µM ATP. On a second tube, 2 mL of D-Luciferin working solution (167 µM, Sigma) was prepared protected from light. The injection system of the luminometer was primed until ready. Following that step, the luminometer software was programmed to set the temperature to 3° C., and under stirring for the duration of the experiment accept 50 µL of sample per condition in a 96-white plate, inject 100 µL of ATP working solution 3 seconds after reading cycle begins; inject 100 µL of D-Luciferin working solution 4 seconds after reading cycle begins and read the luminescence 5 seconds after reading cycle begins. The luciferase luminescence was quantified in a microplate luminometer reader LumiStar Galaxy (BMG Labtech). All conditions were performed in triplicate.

Retinoic Acid Uptake Assay

Experiments were initiated by the addition of medium containing [$^3$H]RA (1 µM and 10 µM) and [$^3$H]RA-NPs (1 µg/mL and 10 µg/mL) to cultures (60,000 cells/condition, 24-well plate, 1 mL) of K562, NB4 and U937 cells. After experimental incubations with medium containing [$^3$H]RA and [$^3$H]RA-NPs for 4, 24 and 72 hours, cells were collected to eppendorfs, washed with PBS by centrifugation (1500 rpm, 5 min, 2 times) to remove non-internalized [$^3$H]RA and then resuspend in 100 µL of lysis buffer (see above) and kept on ice until scintillation counting procedure.

The titrium content of the samples was assayed by adding 100 µL aliquot of the samples to 1 mL liquid scintillation fluid (Packard Ultima Gold) and counted in a TriCarb 2900 TR Scintillation analyzer (Perkin Elmer). All conditions were performed in triplicate.

Time-activation of NPs within cells. NB4 and Zn-induced U937-B412 cells ($6.0 \times 10^4$ cells/condition) were plated in 24-well plates and transfected with $RA^+$ NPs (1 µg/mL) for different time periods (1, 2, 4, 6, 8, 12 and 24 h). The cells were then washed by centrifugation (1300 rpm, 5 min) to remove non-internalized NPs, and immediately exposed to UV light (365 nm, 100 Watts, 5 min). In a second experimental setup, NB4 and Zn-induced U937-B412 cells ($6.0 \times 10^4$ cells/condition) were plated in 24-well plates and transfected with $RA^+$ NPs (1 µg/mL) for 4 h. The cells were then washed by centrifugation (1300 rpm, 5 min) to remove non-internalized NPs, cultured in normal conditions and exposed to UV light (365 nm, 100 Watts, 5 min) at different time points (0, 4, 8, 20 and 44 h). The effect of the intracellular release of RA was evaluated in terms of differentiation of the cells into the myeloid lineage (as assessed by the expression of CD11b) at day 3, as assessed by flow cytometry. All conditions were performed in triplicate.

NB4-RARE cells ($2.5 \times 10^4$ cells/condition) were plated in v-shaped 96-well plates and transfected with $RA^+$ NPs (1 µg/mL) for different time points (1, 2, 4, 6, 8, 12 and 24 h). The cells were then washed by centrifugation (1300 rpm, 5 min) to remove non-internalized NPs, and immediately exposed to UV light (365 nm, 100 Watts, 5 min). For the second experimental setup, NB4-RARE cells ($2.5 \times 10^4$ cells/condition) were plated in v-shaped 96-well plates and transfected with $RA^+$ NPs (1 µg/mL) for 4 h. The cells were then washed by centrifugation (1300 rpm, 5 min) to remove non-internalized NPs, cultured in normal conditions and exposed to UV light (365 nm, 100 Watts, 5 min) at different time points (0, 4, 8, 20 and 44 h). The cells were then cultured for 12 hours after each condition light activation in RPMI-1640 medium supplemented with 10% fetal bovine serum and 100 U/mL PenStrep. After these procedures luciferase luminescence was quantified as described above for the luciferase assays. All conditions were performed in triplicate.

Multiple activation of NPs within cells. Myelocytic differentiation of Zn-induced U937 cells was assessed by the quantification of CD11b expression by flow cytometry. U937-B412 cells ($6.0 \times 10^4$ cells/condition) were cultured with $ZnSO_4$ (0.1 mM) in culture medium up to 24 h prior to experiment to induce the expression of promyelocytic leukemia zinc finger/RARα (PLZF/RARα). Then cells were transfected with $RA^+$ NPs (1 µg/mL) for 4 h, washed, placed in normal culture medium and then different activated by UV light (365 nm, 100 Watts, 5 min). Cells without light activation were used as control. The following conditions were tested: i) single light activation at 4 h; ii) light activations at 4 h and 6 h; iii) light activations at 4 h, 6 h and 8 h and iv) light activations at 4 h, 6 h, 8 h and 10 h. After 3 days, expression of CD11b on U937 cell surface was measured by staining with a fluorescent (PE)-conjugated anti-CD11b mAb (BD Biosciences) using FACS. All conditions were performed in triplicate.

Relative Gene Expression of RAR-α, RAR-β and RAR-γ (Normalized to GAPDH) in Leukemia Cell Lines RNA was extracted using TRIzol® (Ambion) and RNAeasy mini kit (Qiagen) and cDNA was obtained from 1 µg RNA using TaqMan® Reverse Transcription Reagents (Invitrogen), according to supplier's instructions. Gene expression levels of RAR-α, RAR-β and RAR-γ (normalized to GAPDH) in NB4 and U937-B412 Zn-induced or not were quantified with Power SYBR® Green PCR Master Mix using a 7500 Fast Real-Time PCR System (Applied Biosystems, Foster City, USA). Specific primer pairs were SEQ. ID NO:1-CCATCCTCAGAACTCACAA and SEQ. ID NO:2—ACCAGCGAGAATTAATACCT for RAR-α, SEQ. ID NO:3—CACCTAGAGGATAAGCACTT and SEQ. ID NO:4—GGACTCACTGACAGAACA for RAR-β, SEQ. ID NO:5—CCACCTTCTTGCTCCTAC and SEQ. ID NO:6—CTTTCACCCTCTGTTCCT for RAR-γ, SEQ. ID NO:7—AGCCACATCGCTCAGACACC and SEQ. ID NO:8—GTACTCAGCGCCAGCATCG for GAPDH, forward and reverse, respectively. Thermal cycling conditions were 30 s at 94° C., 30 s at 60° C. and 33 s at 72° C., for 40 cycles, followed by a melting curve.

K562 Differentiation Assay

Erythroid differentiation of K562 cells was assessed by cytochemical staining with benzidine solution. K562 cells (6.0×104 cells/condition) were exposed to a wide range of free-RA concentrations for 6 days. Since RA display a very low solubility, DMSO was used to dissolve RA to the culture medium before cell culture experiments (final concentration of DMSO was below 0.01% in culture medium). To investigate the effect of $RA^+$ NPs on K562 differentiation, K562 cells (6.0×104 cells/condition) were transfected with $RA^+$ NPs (from 0.01 up to 10 μg/mL; in serum-free medium) for 4 h, washed by centrifugation (1300 rpm, 5 min) to remove NP excess, and part of the samples exposed to UV light (365 nm, 100 W, 5 min). The cells were then cultured for 6 days in complete medium (RPMI-1640 medium supplemented with 10% FBS (Gibco) and 100 U/mL PenStrep), after which they were stained by a benzidine solution (to stain the heme groups of erythrocytes). The benzidine stock solution was prepared by dissolving benzidine dihydrochloride (20 mg, Sigma) in glacial acetic acid (292 μL) and water (9.7 mL) solution. The working solution was prepared by mixing part of the benzidine stock solution (1 mL) with 30% $H_2O_2$ (20 μL, Panreac). The staining was performed by mixing 50 μL of K562 cells (in the evaluated condition medium) with benzidine working solution at a 1:1 (v/v) ratio, at room temperature for 3 minutes. Following the staining the number of positive cells was determined using a hemocytometer. The staining was performed in three individual experiences for all conditions.

NB4 Differentiation Assay

Myelocytic differentiation of NB4 cells was assessed by quantifying the CD11b expressing population, using flow cytometry. NB4 cells (6.0×$10^4$ cells/condition) were plated in 24-well plates and cultured with soluble RA or light-activatable $RA^+$ NPs. The NPs were suspended in serum free medium and added to cells for 4 h. The cells were then washed by centrifugation (1300 rpm, 5 min) to remove non-internalized NPs, and half of the samples were exposed to UV light (365 nm, 100 W, 5 min). The cells were then cultured for 6 days in RPMI-1640 medium supplemented with 10% FBS (Gibco) and 100 U/mL PenStrep with half medium changes every 3 days. Conditioned medium (CM) was obtained from the centrifugation of $RA^+$ NPs (10 μg/mL) in culture medium for 6 days. After 1, 3 and 6 days, expression of CD11b on NB4 cell surface was measured by FACS using a fluorescent (PE)-conjugated anti-CD11b antibody (BD Biosciences, ICRF44 clone). All conditions were performed in triplicate.

U937 Differentiation Assay

Myelocytic differentiation of U937 cells was assessed by the quantification of CD11b expression by flow cytometry. U937-B412 cells (6.0×$10^4$ cells/condition) were cultured either with or without $ZnSO_4$ (0.1 mM). To induce the expression of PLZF/RARα in U937-B412 cells they were treated for 24 h with $ZnSO_4$ (0.1 mM). Then cells were treated with soluble RA or light-activatable $RA^+$ NPs (transfection for 4 h followed by light activation for 5 min) for 3 days. After 1 and 3 days, expression of CD11b on U937 cell surface was measured by staining with a fluorescent (PE)-conjugated anti-CD11b mAb (BD Biosciences) using FACS. All conditions were performed in triplicate.

AML Differentiation Assay

AML bone marrow mononuclear cells isolated by Ficoll-Histopaque (GE Healthcare) gradient centrifugation, enriched using the MACS CD34 isolation kit (Miltenyi Biotec) and cryopreserved were kindly provided by Dr. Rajeev Gupta (Department of Haematology, UCL Cancer Institute). The isolated $CD34^+$ AML cells were maintained in StemSpan SFEM (Stemcell Technologies) supplemented with a human cytokine cocktail containing SCF (50 ng/mL, Stemcell Technologies), TPO (15 ng/mL) and Flt-3L (50 ng/mL, PeproTech) plus PenStrep (10,000 U/mL, Lonza) and Fungizone (25 μg/mL, Sigma) up to 3 days. Prior to the colony-forming cell (CFC) and long-term culture-initiating cell (LTC-IC) assays, AML cells were incubated for 4 h in Ex-Vivo (Lonza) serum free medium, with and without blank NPs or $RA^+$ NPs in a 24 well plate. After that time, the cells were washed to remove loosely bound NPs. For the CFC assays (2.0×$10^5$ cells/condition) AML cells were plated in triplicate in MethoCult H4230 (3 mL, StemCell Technologies) supplemented with SCF [50 ng/mL], IL-3 [10 ng/mL], and Flt-3L [50 ng/mL], all human, plus PenStrep (10,000 U/mL, Lonza) and Fungizone (25 μg/mL, Sigma) in 6-well plate. For some conditions UV light (365 nm, 100 W, 5 min) was used to activate $RA^+$ NPs. Cultures were scored after 14 days for the presence of clusters and colonies containing >20 cells using an inverted microscope. LTC-IC assays were performed in triplicate in a 6-well plate gelatinized for 2 hours prior to adding the feeders. The feeder layer was composed of a 1:1 mixture of irradiated (80 Gy) SL/SL (1.5×$10^4$ cells/condition) and M210B4 mouse fibroblasts (1.5×$10^4$ cells/condition), kindly provided by Dr. Rajeev Gupta (Department of Haematology, UCL Cancer Institute). AML cells (1×$10^6$ cells/condition) were plated in Myelocult H5100 medium (StemCell Technologies), supplemented with Flt-3L [50 ng/mL], hydrocortisone [$10^{-6}$ M] (StemCell Technologies) and PenStrep (10,000 U/mL, Lonza) and fungizone (25 μg/mL, Sigma). For some conditions UV light (365 nm, 100 Watts, 5 min) was used to trigger RA release. After the cells were inoculated, weekly half medium changes were performed (with Flt-3L [100 ng/mL]) for the duration of the culture. After 5 weeks, all cells were harvested and placed into methylcellulose based assay for the detection of AML-CFC as described above.

In vivo study—All animal work has been conducted according to relevant national and international guidelines and approved by the Bioethics Committee of University of Salamanca. On the day before injecting the cells, PDMS cylindrical constructs (Øinternal=1.0 cm; Øexternal=1.5 cm) were implanted subcutaneously on NOD/SCID mice (Jackson Laboratory) maintained in pathogen-free conditions with irradiated chow. For the ex-vivo activation studies in the day of the experiment, NB4 cells were suspended in serum free medium with (i) no NPs, (ii) with empty NPs (10 μg/mL) or $RA^+$ NPs (10 μg/mL) for 4 h. At the end, cells were washed by centrifugation (1300 rpm, 5 min), and the ones treated with RA⁺ NPs were either activated or not with a blue laser (405 nm, 80 mW) for 5 min. NB4 cells ($5 \times 10^6$ cells per PDMS construct) were injected subcutaneously in the center of the PDMS construct embedded in Matrigel (200 µL, BD Biosciences). Five days after injection of the cells, animals were sacrificed by cervical dislocation and cells within the cylindrical construct were collected and characterized by flow cytometry. For the in vivo activation studies in the day of the experiment, NB4 cells were suspended in serum free medium with (i) no NPs, (ii) with RA⁺ NPs (10 µg/mL) for 4 h. At the end, cells were washed by centrifugation (1300 rpm, 5 min), and $5 \times 10^6$ NB4 cells per PDMS construct were injected subcutaneously in the center of the PDMS construct embedded in Matrigel (200 µL, BD Biosciences). One day after injection, some of both conditions under study were either activated or not with a blue optical fiber (405 nm, 80 mW) for 5 min. Three days after injection of the cells, animals were sacrificed by cervical dislocation and cells within the cylindrical construct were collected and characterized by flow cytometry.

The disclosure is of course not in any way restricted to the embodiments described and a person with ordinary skill in the art will foresee many possibilities to modifications thereof.

The above described embodiments are obviously combinable.

The following claims further set out particular embodiments of the disclosure.

The invention claimed is:

1. A light-activatable nanoparticle for the transportation and release of an active substance, comprising:
   a polycation;
   a polyanion;
   and 4,5-dimethoxy-2-nitrobenzyl chloroformate as a light-sensitive photochrome attached to the polycation or the polyanion, wherein said photochrome is hydrophobic and suitable to photo-cleave when activated by an irradiation source.

2. The nanoparticle according to claim 1, wherein said polycation is a polymer.

3. The nanoparticle according to claim 1, wherein said polycationic polymer is selected from: poly(ethyleneimine), polylysine, poly(amino ester)s, poly(disulfide amines), chytosan, or combinations thereof.

4. The nanoparticle according to claim 1, wherein the polyanion is selected from: dextran sulphate, polyaspartic acid, hyaluronic acid, or combinations thereof.

5. The nanoparticle according to claim 1, wherein:
   poly(ethyleneimine) (PEI) is the polycation; and
   dextran sulphate is the polyanion.

6. The nanoparticle according to claim 5, wherein the said active substance is selected from the group consisting of: a cellular modulation agent, a differentiating agent, a metabolic regulator, a cell cycle regulator, an epigenetic regulator, a reprogramming agent, a transcription factor, and combinations thereof.

7. The nanoparticle according to claim 6, wherein the said active substance is retinoic acid.

8. The nanoparticle according to claim 7, wherein molar ratio of DMNC to PEI is between 1% and 100%.

9. The nanoparticle according to claim 8, wherein the final degree of substitutions PEI-DMNC is between 20-100%.

10. The nanoparticle according to claim 1, wherein the average diameter of the nanoparticle is between 1-1000 nm.

11. The nanoparticle according to claim 1, wherein said irradiation source is UV light or a blue laser.

12. A method of treatment of cancer diseases or for transfecting stem cells, comprising providing the nanoparticle according to claim 1 to a human.

13. A composition comprising a plurality of the nanoparticles of claim 1, in a concentration of nanoparticle up to 100 µg/mL.

14. The composition according to claim 13, wherein the composition is a topic formulation or an injectable formulation.

15. A method for obtaining a light-activatable polymeric nanoparticle, comprising the following steps:
   derivatizing a polycation polymer with a light-sensitive hydrophobic photochrome in dimethyl sulfoxide, DMSO;
   precipitating said polycation-photochrome solution into an aqueous solution comprising polyanion; and
   separating the nanoparticles from the remaining polymers.

16. The method according to claim 15, further comprising the following steps:
   derivatizing poly(ethyleneimine) with 4,5-dimethoxy-2-nitrobenzyl chloroformate in DMSO, in presence of triethylamine;
   precipitating PEI-DMNC solution into an aqueous solution of dextran sulphate.

17. The method according to claim 16, further comprising adding zinc sulfate.

18. The nanoparticle according to claim 8, wherein the final degree of substitutions PEI-DMNC is between 25-50%.

19. The nanoparticle according to claim 1, wherein the average diameter of the nanoparticle is 160 nm.

20. The method of claim 15, wherein the nanoparticles are separated from the remaining polymers by centrifugation or dialysis.

* * * * *